US009435765B2

(12) United States Patent
Reimitz et al.

(10) Patent No.: US 9,435,765 B2
(45) Date of Patent: Sep. 6, 2016

(54) CARTRIDGE AND SYSTEM FOR MANIPULATING SAMPLES IN LIQUID DROPLETS

(71) Applicant: TECAN TRADING AG, Mannedorf (CH)

(72) Inventors: S. Nicholas Reimitz, Campbell, CA (US); Bruce Richardson, Los Gatos, CA (US); Marc N. Feiglin, East Brunswick, NJ (US); Anne R. Kopf-Sill, Portola Valley, CA (US)

(73) Assignee: Tecan Trading AG, Mannedorf (CH)

( * ) Notice: Subject to any disclaimer, the term of this patent is extended or adjusted under 35 U.S.C. 154(b) by 713 days.

(21) Appl. No.: 13/737,183

(22) Filed: Jan. 9, 2013

(65) Prior Publication Data

US 2013/0118900 A1    May 16, 2013

Related U.S. Application Data

(63) Continuation-in-part of application No. 13/188,584, filed on Jul. 22, 2011, now Pat. No. 8,470,153.

(51) Int. Cl.
*G01N 27/447* (2006.01)
*B01L 3/00* (2006.01)
*B01L 7/00* (2006.01)

(52) U.S. Cl.
CPC ... *G01N 27/44782* (2013.01); *B01L 3/502738* (2013.01); *B01L 3/502792* (2013.01); *B01L 3/5029* (2013.01); *B01L 3/502715* (2013.01); *B01L 3/523* (2013.01); *B01L 3/527* (2013.01); *B01L 7/52* (2013.01); *B01L 2200/025* (2013.01);*B01L 2200/027* (2013.01); *B01L 2200/04*(2013.01); *B01L 2200/0647* (2013.01);B01L 2200/141 (2013.01); *B01L*

(Continued)

(58) Field of Classification Search
CPC .................. B01L 2200/25; B01L 2200/027; B01L 2200/04; B01L 3/502715; B01L 3/502738; B01L 3/502792; B01L 3/523; B01L 3/527; B01L 2300/044; B01L 2300/0672; B01L 2300/0681; B01L 2300/0829; B01L 2300/0864; B01L 2300/0867; B01L 2300/0887; B01L 2300/089; B01L 2300/161; B01L 2400/0427; B01L 2400/043; B01L 2400/0478; G01N 27/44791; G01N 27/44782
See application file for complete search history.

(56) References Cited

U.S. PATENT DOCUMENTS

| 5,486,337 A | 1/1996 | Ohkawa |
| 6,565,727 B1 | 5/2003 | Shenderov |
| 2002/0043463 A1 | 4/2002 | Shenderov |
| 2007/0217956 A1 | 9/2007 | Pamula et al. |

FOREIGN PATENT DOCUMENTS

| EP | 1 518 604 | 3/2005 |
| EP | 1 722 234 | 11/2006 |

(Continued)

*Primary Examiner* — Luan Van
*Assistant Examiner* — Maris R Kessel
(74) *Attorney, Agent, or Firm* — Notaro, Michalos & Zaccaria P.C.

(57) ABSTRACT

A cartridge manipulates samples in liquid droplets with an electrode array when a working film is placed on the array. The cartridge has a body with lower surface and wells to hold samples, each with a bottom opening to release liquid. A piercable bottom structure seals the bottom openings. A working film below the body has a hydrophobic upper surface. A peripheral spacer connects the working film to the body and forms a gap is between the body and surface. A top piercing system located in at least one of the wells has a piston and a piercing element, the piston being movable in the well and the piercing element piercing the piercable bottom structure for releasing a sample from a well into the gap.

23 Claims, 7 Drawing Sheets

(52) U.S. Cl.
CPC ........................................ *2300/044* (2013.01); *B01L 2300/0672* (2013.01); *B01L 2300/0681* (2013.01); *B01L 2300/089* (2013.01); *B01L 2300/0829* (2013.01); *B01L 2300/0864* (2013.01); *B01L 2300/0867* (2013.01); *B01L 2300/0887* (2013.01); *B01L 2300/161* (2013.01); *B01L 2400/043* (2013.01); *B01L 2400/0427* (2013.01); *B01L 2400/0478* (2013.01); *B01L 2400/0683* (2013.01)

(56) References Cited

FOREIGN PATENT DOCUMENTS

| | | |
|---|---|---|
| EP | 2 548 646 | 1/2013 |
| WO | WO 2007/061943 | 5/2007 |
| WO | WO 2007/112114 | 10/2007 |
| WO | WO 2009/052095 | 4/2009 |
| WO | WO 2009/111769 | 9/2009 |
| WO | WO 2009/137415 | 11/2009 |
| WO | WO 2010/069977 | 6/2010 |
| WO | WO 2011/084703 | 7/2011 |

CARTRIDGE AND SYSTEM FOR MANIPULATING SAMPLES IN LIQUID DROPLETS

CROSS-REFERENCE TO RELATED APPLICATIONS

This application is a continuation-in-part application based on the U.S. patent application Ser. No. 13/188,584. This application further relates to the U.S. patent application Ser. No. 13/304,481. All cited applications are hereby incorporated by reference in their entirety.

FIELD OF TECHNOLOGY

The present invention relates to a cartridge with a polymer film for manipulating samples in liquid droplets thereon and at least one piercing element for releasing a reagent or sample onto the polymer film. The invention further relates to a liquid droplet manipulation system comprising such a cartridge, an electrode array supported by a substrate, and a central control unit for controlling the selection of individual electrodes and for providing them with individual voltage pulses for manipulating liquid droplets by electrowetting.

The analysis of biological material such as tissue samples or microorganisms, in particular nucleic acids or proteins, is well established in various fields, especially in the field of scientific research, pharmacological screening or forensic sciences, and medical diagnostics. Adequate methods have been developed for different purposes, each method requiring a special set of reaction reagents and devices for the performance of the respective method. However it remains a challenge to adopt existing analysis procedures to the different conditions and requirements present in each field. For example in criminal forensics, a relatively small amount of material to be analyzed is usually available. Additionally, the quality of such material can be rather low, placing additional challenges on the involved personnel. Thus, the procedures need to be specifically adapted to these conditions. On the other hand, for laboratory diagnostic procedures the biological material is usually available in sufficient amounts, but the required methods are to be adopted individually depending on the underlying question to be solved.

For the first steps of the analysis of biological material, there are methods required, which per se are well known in the art. Material of interest is collected e.g. from a crime scene (in criminal forensics) or from a patient (for diagnostic purposes). Such materials can be tissue samples (such as oral mucosa cells, hair follicles) or bodily fluids (such as blood, sputum, etc.). This starting material then requires further processing to make nucleic acids or proteins available for the analysis. Typically, a lysis step is initially applied for these purposes, involving for example the application of heat, a certain enzymatic activity, and/or the application of specific chemicals. The cell lysis is followed by a purification of the nucleic acid or protein of interest from the additional cellular material. In the case where the nucleic acid is to be analyzed, an amplification step might be advisable to increase the sample yield. Nucleic acid amplification is typically achieved by the polymerase chain reaction (PCR). This method allows the amplification of specific, predefined nucleic acid sequences by the use of sequence-specific primer. Depending on the question to be solved, the amplified material might be further analyzed for example by sequencing.

With the progresses in the reliability and simplification of such methods, for example by the use of kits, these methods have become standard procedures in these different fields. Together with an increasing demand for diagnostics based on molecular level, there is an increasing need for the automated processing of relevant samples, starting with an initial biological sample through to the final analysis.

RELATED PRIOR ART

Automated liquid handling systems are generally well known in the art. An example is the Freedom EVO® robotic workstation from the present applicant (Tecan Schweiz A G, Seestrasse 103, CH-8708 Männedorf, Switzerland). This device enables automated liquid handling in a stand-alone instrument or in automated connection with an analytical system. These automated systems typically require larger volumes of liquids (microliter to milliliter) to process. They are also larger systems that are not designed to be portable.

A portable device for lysing and/or purifying biological samples is known from WO 2007/061943. The processing of nucleic acids is performed within a cartridge chamber using electrodes arranged on the two sides, thus processing biological material by electrolysis, electroporation, electroosmosis, electrical kinetic or resistive heating. The cartridge further comprises sieving matrixes or membranes. By the use of adequate buffers and other reagents, in combination with the application of the electrodes, various reactions can be performed within the chamber, and desired products can be directed for example to collecting membranes. If the sequences of nucleic acids are analyzed, the number of sequences analyzed in parallel is limited to the number of probes. Typically, the number of probes that can be worked on is limited to four different wavelengths that an associated instrument can detect in parallel. The cartridge itself can be placed into an integrated system comprising the required control elements and energy sources. Although this cartridge provides a system to at least partially control the sample processing electronically, intervention of an investigator or of technical lab staff is still required.

Other approaches to deal with the automated processing of biological samples originate from the field of microfluidics. This technical field generally relates to the control and manipulation of liquids in a small volume, usually in the micro- or nanoscale format. Liquid movement in a channel system is known per se as, e.g. being controlled by micro pumps in stationary devices or centripetal forces in rotating labware. In digital microfluidics, a defined voltage is applied to electrodes of an electrode array, so that individual droplets are addressed (electrowetting). For a general overview of the electrowetting method, please see Washizu, IEEE Transactions on Industry Applications, Volume 34, No. 4, 1998, and Pollack et al., Lab chip, 2002, Volume 2, 96-101. Briefly, electrowetting refers to a method to move liquid droplets using arrays of microelectrodes, preferably covered by a hydrophobic layer. By applying a defined voltage to electrodes of the electrode array, a change of the surface tension of the liquid droplet, which is present on the addressed electrodes, is induced. This results in a remarkable change of the contact angle of the droplet on the addressed electrode, hence in a movement of the droplet. For such electrowetting procedures, two principle ways to arrange the electrodes are known: using one single surface with an electrode array for inducing the movement of droplets or adding a second surface that is opposite a similar electrode array and that provides at lest one ground electrode. A major advantage of the electrowetting technology is that only a small volume of liquid is required, e.g. a single droplet. Thus, liquid processing can be carried out within considerably shorter time.

Furthermore the control of the liquid movement can be completely under electronic control resulting in automated processing of samples.

A device for liquid droplet manipulation by electrowetting using one single surface with an electrode array (a monoplanar arrangement of electrodes) is known from the U.S. Pat. No. 5,486,337. All electrodes are placed on a surface of a carrier substrate, lowered into the substrate, or covered by a non-wettable surface. A voltage source is connected to the electrodes. The droplet is moved by applying a voltage to subsequent electrodes, thus guiding the movement of the liquid droplet above the electrodes according to the sequence of voltage application to the electrodes.

An electrowetting device for microscale control of liquid droplet movements, using and electrode array with an opposing surface with at least one ground electrode of is known from U.S. Pat. No. 6,565,727 (a biplanar arrangement of electrodes). Each surface of this device may comprise a plurality of electrodes. The drive electrodes of the electrode array are preferably arranged in an interdigitated relationship with each other by projections located at the edges of each single electrode. The two opposing arrays form a gap. The surfaces of the electrode arrays directed towards the gap are preferably covered by an electrically insulating, hydrophobic layer. The liquid droplet is positioned in the gap and moved within a non-polar filler fluid by consecutively applying a plurality of electric fields to a plurality of electrodes positioned on the opposite sites of the gap.

The use of such an electrowetting device for manipulating liquid droplets in the context of the processing of biological samples is known from the US patent application No. 2007/0217956 A1. Here it is suggested to amplify nucleic acids on a printed circuit board for example through thermocycling. The droplets are transported on an array of electrodes by applying a potential between a reference electrode and one or more drive electrodes. The sample is placed into a reservoir on the printed circuit board, and droplets are dispensed on said printed circuit board.

However, none of the above cited devices allow the fully automated processing of nucleic acids starting from collected material up to the final analysis in the small volume scale. An additional disadvantage of the presented devices comes with the nature of such arrangements of electrode arrays, being generally expensive in production, thus being rather non-disposable in use. A continuous re-use of the same device for different biological samples and applications however bears the risk of cross-contaminating the samples of interest, which could lead to false results. Therefore, such devices are not suited for high-throughput assays.

Containers with a polymer film for manipulating samples in liquid droplets thereon are known from WO 2010/069977 A1: A biological sample processing system comprises a container for large volume processing and a flat polymer film with a lower surface and a hydrophobic upper surface. The flat polymer film is kept at a distance to a base side of the container by protrusions. This distance defines at least one gap when the container is positioned on the film. A liquid droplet manipulation instrument comprises at least one electrode array for inducing liquid droplet movements. A substrate supporting the at least one electrode array is also disclosed as well as a control unit for the liquid droplet manipulation instrument. The container and the film are reversibly attached to the liquid droplet manipulation instrument. The system thus enables displacement of at least one liquid droplet from the at least one well through the channel of the container onto the hydrophobic upper surface of the flat polymer film and above the at least one electrode array. The liquid droplet manipulation instrument is accomplished to control a guided movement of said liquid droplet on the hydrophobic upper surface of the flat polymer film by electrowetting and to process there the biological sample.

For providing liquids to the electrowetting process, it is desirable to store a respective liquid already in the corresponding electrowetting system. In this way, the liquid may be provided for droplet generation and manipulation at the time and place where appropriate and required. However, when storing liquids directly in the electrowetting device, mechanisms are required which allow on the one hand a safe storage without the stored liquid leaking out when the device is e.g. moved or transported. On the other hand, release of the liquid shall be enabled in a reliable and simple manner that allows the instrument and cartridge to be low-cost but without losing safety during storage.

An instrument for manipulating liquid samples using electrowetting technique and including a liquid storage and release mechanism is known from WO 2009/111769 A2. Here, the top substrate of a droplet actuator, which is positioned above the electrode array for forming a gap, comprises one or more reservoirs for storing liquid samples. The stored liquid may be released into the gap via a lower opening in the gap. For closing the reservoir toward the gap, a plug or another removable barrier is located within that opening, which may be punctured, removed or dissolved for releasing the liquid flow path to the gap, the plug. The upper opening may be sealed by a removable cap. In particular in view of the relatively small size of such a droplet actuator and included liquid reservoirs and openings, using a tiny plug and cap provides a rather complicated solution for closing and opening the reservoir.

OBJECTS AND SUMMARY OF THE PRESENT INVENTION

It is an object of the present invention to suggest an alternative cartridge with a working film and at least one piercing element for manipulating samples in liquid droplets with an electrode array when the working film of the cartridge is placed thereon. It is another object of the present invention to suggest an appropriate liquid droplet manipulation system with an electrode array on which the inventive cartridge can be positioned for manipulating samples in liquid droplets on the working film of the inventive cartridge.

This object is achieved according to a first aspect in that a cartridge is suggested with a working film and at least one piercing element for manipulating samples in liquid droplets with an electrode array when the working film of the cartridge is placed on said electrode array. The invention is characterized in that the cartridge comprises:

a) a body that comprises an upper surface, a lower surface, and a number of wells configured to hold therein reagents or samples, each well comprising a top opening, and a bottom opening for releasing a liquid from the well;
b) a piercable bottom structure impermeable to liquids and configured to seal at least one of the bottom openings of the wells;
c) a working film located below the lower surface of the body, the working film being impermeable to liquids and comprising a hydrophobic upper surface;
d) a peripheral spacer located below the lower surface of the body and connecting the working film to the body; and e) a gap between the lower surface of the body and the hydrophobic upper surface of the working film, the gap being defined by the peripheral spacer.

The cartridge according to the invention further comprises:

f) at least one top piercing system, each located within at least one of the wells for releasing a reagent or sample from said at least one well into the gap;

wherein each top piercing system comprises a piston and a piercing element, the piston being configured to be movable within said well while providing a seal between the piston and the inner wall of the well, and the piercing element being configured as a thorn located at a lower side of the piston and being configured to pierce the piercable bottom structure for releasing a reagent or sample from said at least one well into the gap upon moving the piston within the well toward its bottom opening.

This object is achieved according to a second aspect in that a liquid droplet manipulation system comprising a substrate and an electrode array is suggested on top of which the inventive cartridge can be positioned for manipulating samples in liquid droplets on the working film of the inventive cartridge and for releasing a liquid droplet onto the working film. The system further comprises a central control unit for controlling the selection of individual electrodes of the electrode array and for providing the electrodes with individual voltage pulses for manipulating liquid droplets by electrowetting.

Additional and inventive features derive from the dependent claims in each case.

Advantages of the Cartridge According to the Present Invention Comprise:

The cartridge is designed to physically match for numerous different assays and is therefore generic for a variety of different assays.

The disposable cartridge is designed for single use only and is provided preloaded with prepared treatment liquids and/or reagents in a number and quantity sufficient for the planned assay.

The cartridge is designed for safe intake of specimens such as a buccal swab head, a piece of tissue or blotting paper, liquid samples like blood and the like.

The electrode array is completely separate from the cartridge and can be reused a very large number of times.

The electrode array preferably is of variable design according to the assay that is to be carried out.

The electrode array is not touched by specimen material, samples, or reagents and is thus clean at all times.

With the cartridge and system according to the invention, a single sample can be split into multiple droplets. This enables:

individual manipulation of single droplets;

performing separate reactions in each one of these droplets;

processing each droplet differently and individually; e.g. nucleic acid amplification can be performed and different Single Nucleotide Polymorphism (SNP) can be analyzed in nucleic acid samples in each droplet;

some of the droplets of a sample can be processes for nucleic acid analysis and other droplets from the same sample can be provided for an immunoassay or reference samples;

analysis of a large number of droplets can be performed with the application of a single wavelength, e.g. the number of sequences analyzed in parallel is only limited by the common area of the cartridge and system according to the invention and not by the instrument optics.

Liquid reagents or samples may be stored and released inside the cartridge in a simple and safe manner, so that required reagents are available for a manipulation process at the required time without the need of disrupting the process by a complicated pipetting process which might involve the separating the cartridge from the electrode array.

Liquid reagents or samples are kept inside a cartridge throughout all experiments and then safely discarded together with the cartridge.

BRIEF DESCRIPTION OF THE DRAWINGS

The cartridge and system for manipulating samples in liquid droplets according to the present invention are now explained in more detail with the help of the attached drawings that show preferred, exemplary embodiments relating to the invention (FIGS. 1 to 9) and according to the present invention (FIGS. 10 to 14) and that are not intended to narrow the scope of the invention. It is shown in:

FIG. 8 detailed 3D views of the specimen intake of a frame-like cartridge according to the third or fourth related embodiment, wherein it is shown in:

FIG. 11 an overview of the different selected embodiments of the top piercing system according to the present invention, wherein it is shown in:

FIG. 12 an overview of different selected embodiments of the thorn, wherein it is shown in:

FIG. 13 a vertical cross section through a plate-like structured cartridge, with a working film and two exemplarily shown wells, each having a top piercing system; the cartridge being almost in contact with the electrode array of a system for liquid droplet manipulation and being enwrapped by an elongated working film for protection; the cartridge comprising the piercable bottom structure configured as a piercable bottom foil, a cover layer for the gap and a thorn relief spacer layer arranged in-between;

DESCRIPTION OF PREFERRED EMBODIMENTS OF THE INVENTION

Figure 1:
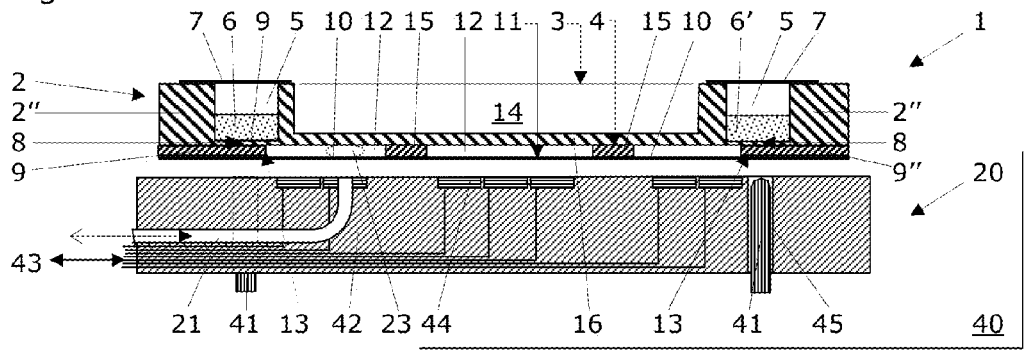
FIG. 1 a vertical cross-section through a frame structured cartridge according to a first related embodiment with a central opening closed by a bottom portion, with a number of wells and a working film contacted by a separate peripheral spacer; the cartridge is almost in contact with the electrode array of a system for liquid droplet manipulation.

The FIG. 1 shows a vertical cross-section through a frame structured cartridge 1 according to a first related embodiment with a central opening 14 closed by a bottom portion 16, with a number of wells 5 and a working film 10 contacted by a peripheral spacer 9 that is configured as a separate peripheral element 9". The cartridge 1 is almost in contact with the electrode array 20 of a system 40 for liquid droplet manipulation.

This cartridge 1 comprises a working film 10 for manipulating samples in liquid droplets with an electrode array 20 when the working film 10 of the cartridge 1 is placed on said electrode array 20. This cartridge 1 also comprises a body 2, which body 2 preferably comprises an essentially flat lower surface 4. According to the first related embodiment, the body 2 is configured as a frame structure 2" with a central opening 14. The body 2 comprises an upper surface 3, a lower surface 4, and a number of wells 5 configured to hold therein reagents 6 or samples 6'. Preferably the material of the body 2 is of an inert plastic material that is impermeable to liquids and that does not take up or interfere with the liquids or samples contained in the wells 5. Preferred materials for injection molding of the body 2 in the form of a frame structure 2" comprise cyclic olefin copolymer (COC), cyclic olefin polymer (COP), polypropylene, polystyrene, polycarbonate, and glass. Preferred production techniques other than injection molding comprise cutting and/or punching of e.g. polytetrafluorethylene or polytetrafluorethen (PTFE).

This cartridge 1 also comprises a flexibly deformable top structure 7 that is impermeable to liquids and that is configured to seal a top side of the wells 5. Preferably an as depicted, the flexibly deformable top structure 7 is configured as a flexible foil that is sealingly attached to the upper surface 3 of the frame structure 2". The flexible foil preferably is made of an elastomeric material, such as a rubber or a thermoplastic elastomer (TPE) membrane and preferably is sealingly attached to the upper surface 3 of the frame structure 2" by welding. Alternatively, the flexibly deformable top structure 7 is configured as a flexible top portion of the body 2 that is integrated in the frame structure 2" (not shown). In this case, the body material preferably is TPE.

Figure 10:
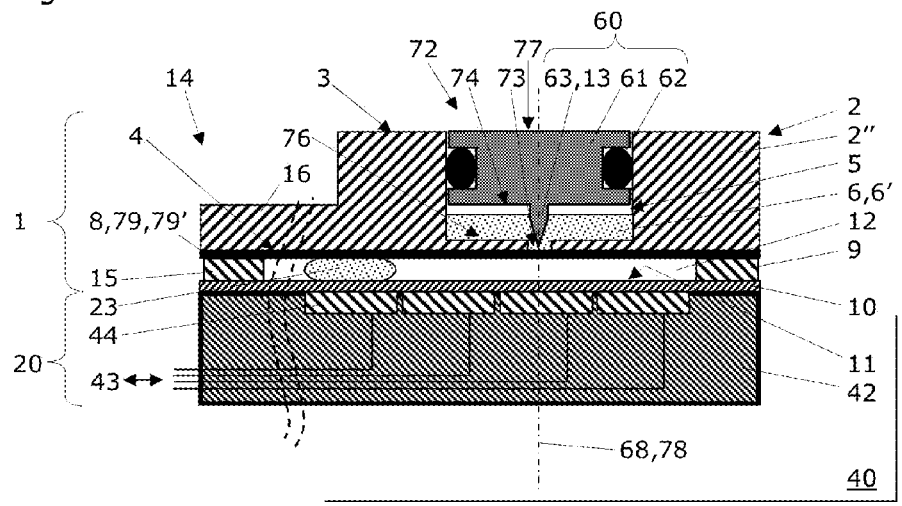
FIG. 10 a vertical cross section through a frame structured cartridge in a fifth embodiment and according to the present invention having a central opening across the body closed by a bottom portion of the body, with a working film and one exemplarily shown well having a top piercing system according to a first embodiment; the cartridge is in contact with the electrode array of a system for liquid droplet manipulation; the piercable bottom structure is configured as a piercable bottom foil.

This cartridge 1 also comprises a piercable bottom structure 8 that is impermeable to liquids and that is configured to seal a bottom side of the wells 5. As depicted here, the piercable bottom structure 8 is configured as a piercable bottom portion of the body 2 that is integrated in frame structure 2". In this case, the body material preferably is TPE. Alternatively, the piercable bottom structure 8 is configured as a piercable foil that is sealingly attached to the lower surface 4 of the frame structure 2" (as shown in FIG. 10). In this case, the piercable foil preferably is made of an elastomeric material, such as a rubber or a thermoplastic elastomer (TPE) membrane.

This cartridge 1 also comprises a working film 10 that is located below the lower surface 4 of the body 2,2". The working film 10 is impermeable to liquids and comprises a hydrophobic upper surface 11, on which the droplets are to be moved by electrowetting techniques.

According to a first preferred embodiment, the working film 10 is configured as a monolayer of a hydrophobic material:

In the preferred embodiment depicted in FIG. 1, the monolayer of hydrophobic material is also electrically insulating (so that the working film 10 electrically isolates each one of the individual electrodes 44 of the electrode array 20). Thus, the cartridge 1 can directly be placed with its working film 10 on top of the electrode array 20 without any need of an additional dielectric layer. Preferred materials for producing such a preferred dielectric/hydrophobic working film 10 are selected from the group comprising fluorinated ethylene propylene (FEP) such as perfluorethylenepropylene copolymer; perfluoralcoxy polymers and copolymers (PFA); cyclic olefin polymers and copolymers (COP); and polyethylene (PE).

If the monolayer of hydrophobic material however is not electrically insulating (so that working film 10 would cause shortage between the individual electrodes 44 of the electrode array 20) the cartridge 1 must be placed with its working film 10 on top of the electrode array 20 with an additional dielectric layer located between the electrode array 20 and the working film 10 (not shown). Such an additional dielectric layer could be attached to the lower surface of the working film 10 or to the upper surface or surface level 48 of the individual electrodes 44 (not shown). Alternatively, an additional dielectric layer could be provided as a separate dielectric sheet that is to be positioned on the electrode array 20 before the cartridge 1 is placed thereon with its working film 10 (not shown). A preferred material for producing such a working film 10 of a monolayer of hydrophobic non-dielectric material is for example polytetrafluorethylene or polytetrafluorethen (PTFE).

According to a second preferred embodiment, the working film 10 is configured as a monolayer of electrically non-conductive material of which the upper surface 11 is treated to be hydrophobic. The cartridge 1 can directly be placed with its working film 10 on top of the electrode array 20 without any need of an additional dielectric layer. Such treatment can be coating the monolayer of electrically non-conductive material with silanes (Marcia Almanza-Workman et al. 2002).

According to a third preferred embodiment, the working film 10 is configured as a laminate comprising a lower layer and a hydrophobic upper layer, the lower layer being electrically conductive or non-conductive:

Similar as shown in FIG. 1, the laminate of the working film 10 preferably comprises a dielectric lower layer and a hydrophobic upper layer, so that the working film 10 electrically isolates each one of the individual electrodes 44 of the electrode array 20. Alternatively, a third layer of hydrophobic material can be laminated to the lower side of the dielectric layer so that a sandwich is formed comprising a dielectric layer that is located between two hydrophobic layers. In any case, the cartridge 1 can directly placed with its working film 10 on top of the electrode array 20 without any need of an additional dielectric layer. Preferred material combinations for producing such a preferred laminate working film 10 comprising at least one dielectric and at least one hydrophobic layer are e.g. selected from fluorinated ethylene propylene (FEP) such as perfluorethylenepropylene copolymer for the hydrophobic layer and polyimides (PI) like Kapton® of DuPont for the dielectric layer.

If however the laminate of the working film 10 comprises a lower layer of a non-dielectric material (so that working film 10 would cause shortage between the individual electrodes 44 of the electrode array 20) the cartridge 1 must be placed with its working film 10 on top of the electrode array 20 with an additional dielectric layer located between the electrode array 20 and the working film 10. Such an additional dielectric layer could be attached to the lower surface of the working film 10 or to the upper surface or surface level 48 of the individual electrodes 44 (not shown). Alternatively, an additional dielectric layer could be provided as a separate dielectric sheet that is to be positioned on the electrode array 20 before the cartridge 1 is placed thereon with its working film 10 (not shown).

If there actually is a need to place an additional dielectric layer between the electrode array 20 of a system 40 for liquid droplet manipulation and the working film of the cartridge according to the present invention or if there is no such need, it may be preferred to cover the electrode array with an additional dielectric layer just in order to facilitate cleaning of the electrode array 20 of a system 40 for liquid droplet manipulation and for protecting the individual electrodes from being wetted (electrically connected) oxidation or damage.

This cartridge 1 also comprises a peripheral spacer 9 that is located below the lower surface 4 of the body 2,2',2" and that connects the working film 10 to the body 2,2',2". This cartridge 1 also comprises a gap 12 between the lower surface 4 of the body 2,2',2" and the hydrophobic upper surface 11 of the working film 10. This gap 12 is defined by the peripheral spacer 9. Preferably, the peripheral spacer 9 is configured as a peripheral rim 9' that surrounds an area of the gap 12 and that is integrally formed with the body 2 (see FIG. 2). Alternatively and as shown in FIG. 1, the peripheral spacer 9 is configured as a separate peripheral element 9" that surrounds the gap 12 and that is attached to the lower surface 4 of the body 2 that here is configured as a frame structure 2". As depicted, the working film 10 preferably is attached to the separate peripheral element 9" of the frame structure 2".

Preferably, and as large and numerous as necessary, the cartridge 1 comprises intermediate spacers 15 that are located within the area of the gap 12 and that are attached to the lower surface 4 of the body 2 of the frame structure 2". These intermediate spacers preferably have the same height as the separate peripheral element 9" and preferably define the same gap dimension.

This cartridge 1 also comprises a number of piercing elements 13 that are located below piercable bottom structures 8 and that are configured to pierce the piercable bottom structures 8 for releasing reagents or samples 6,6' from the wells 5 into the gap 12. In the embodiment of the cartridge as depicted in FIG. 1, the piercing elements 13 are located within the area of the gap 12 and are integrally formed with the spacer 9 that is configured as a separate ring-like element 9" and that surrounds the gap 12. Preferably, the piercing elements 13 are located below a well 5 or an intake recess and are configured to pierce at least the piercable bottom structure 8 when actuated by an actuating element 41 of a system 40 for liquid droplet manipulation. The actuating elements 41 preferably are guided in their movements by a guiding channel 45.

Preferably, the central opening 14 of the frame structure 2" is configured as a depression in the upper surface 3 of the body 2 leaving a bottom portion 16 of the body 2 that is integrally formed with the frame structure 2" to form the substantially flat lower surface 4 of the body 2. Therefore, it is shown in FIG. 1 that the gap 12 extends between the lower surface 4 of the body 2 and the upper, hydrophobic surface 11 of the working film 10.

Figure 2:
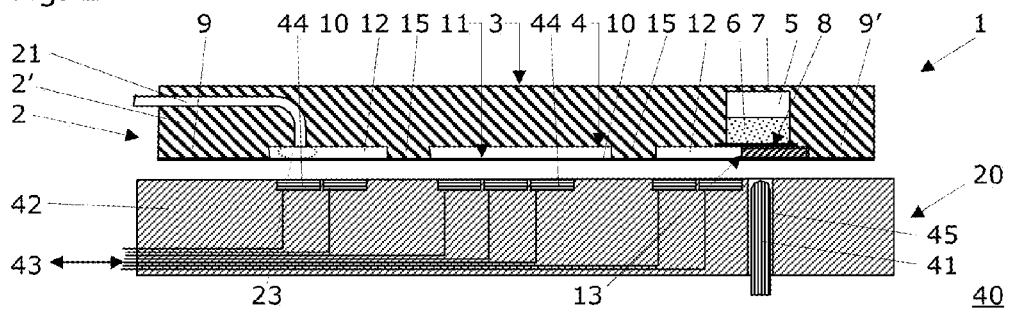
FIG. 2 a vertical cross-section through a plate-like structured cartridge according to a second related embodiment with a number of wells and a working film contacted by an integrated peripheral rim; the cartridge is almost in contact with the electrode array of a system for liquid droplet manipulation.

Preferably, the substrate 42 comprises at least one optical fiber 21 for bringing light to a droplet 23 (here only indicated in dotted lines) in the gap 12 and/or for guiding light away from a droplet 23 in the gap 12. In FIG. 1, a so called bottom reading optical system is indicated by the optical fiber 21. With this optical system, excitation light (originating from a light source (not shown) can be brought through an individual electrode 44 that is optically transparent (not shown) or that comprises a through hole (shown). The excitation light then penetrates the working film 10 that needs to be optically transparent and enters the droplet 23 with sample material in it. If the sample material comprises a fluorophor, this fluorophor will emit fluorescence that then is detected by the optical bottom reading system and a detector connected to the latter. Accordingly, the bottom reading system in the embodiment shown in FIG. 1 is configured to send excitation light to the sample and to receive and detect fluorescence emitted by the sample. Preferably the optical fiber 21 is integrated into the substrate 42 of the electrode array 20 of the system 40 for the manipulation of droplets. This substrate also comprises electrical lines that link the individual electrodes 44 with a central control unit 43 of the system 40. FIG. 2 shows a vertical cross-section through a cartridge 1 with a body 2 that is configured as a plate-like structure 2' according to a second related embodiment. This cartridge 1 comprises a number of wells 5 and a working film 10 that is contacted to the body 2 by an integrated peripheral rim 9'. The cartridge 1 is almost in contact with the electrode array 20 of a system 40 for liquid droplet manipulation.

This cartridge 1 also comprises a working film 10 for manipulating samples in liquid droplets with an electrode array 20 when the working film 10 of the cartridge 1 is placed on said electrode array 20. This cartridge 1 also comprises a body 2, which body 2 preferably comprises an essentially flat lower surface 4. According to the second embodiment, the body 2 is configured as a plate-like structure 2'. The body 2 comprises an upper surface 3, a lower surface 4, and a number of wells 5 configured to hold therein reagents 6 or samples 6'. Like for the frame structure of the first embodiment, the material of the body 2 preferably is of an inert plastic material that is impermeable to liquids and that does not take up or interfere with the liquids or samples contained in the wells 5. The same plastic materials for injection molding of the body 2 as for the frame structure 2" are also preferred for producing the plate-like structure 2' of this embodiment.

This cartridge 1 also comprises a flexibly deformable top structure 7 that is impermeable to liquids and that is configured to seal a top side of the wells 5. Preferably an as depicted in FIG. 2, the flexibly deformable top structure 7 is configured as a flexible top portion of the body 2 that is integrated in the plate-like structure 2'. The material for injection molding of the body 2 and it's flexible top portion preferably is TPE. Alternatively, the flexibly deformable top structure 7 is configured as a flexible foil that is sealingly attached to the upper surface 3 of the plate-like structure 2'. The flexible foil preferably is made of an elastomeric material, such as a rubber or a thermoplastic elastomer (TPE) membrane and preferably is sealingly attached to the upper surface 3 of the plate-like structure 2' by welding.

This cartridge 1 also comprises a piercable bottom structure 8 that is impermeable to liquids and that is configured to seal a bottom side of the wells 5. Preferably and as depicted, the piercable bottom structure 8 is configured as a piercable foil that is sealingly attached to the lower surface 4 of the plate-like structure 2'. This piercable foil preferably is made of an elastomeric material, such as a rubber or a thermoplastic elastomer (TPE) membrane. Alternatively, the piercable bottom structure 8 is configured as a piercable bottom portion of the body 2 that is integrated in the plate-like structure 2' (not shown). In this case, the body material preferably is TPE.

This cartridge 1 also comprises a working film 10 that is located below the lower surface 4 of the body 2,2". The working film 10 is impermeable to liquids and comprises a hydrophobic upper surface 11, on which the droplets are to be moved by electrowetting techniques. All embodiments of the working film 10 as well as the additional dielectric layer as described in connection with FIG. 1 are also preferred for the cartridge depicted in FIG. 2.

This cartridge 1 also comprises a peripheral spacer 9 that is located below the lower surface 4 of the body 2,2',2" and that connects the working film 10 to the body 2,2',2". This cartridge 1 also comprises a gap 12 between the lower surface 4 of the body 2,2',2" and the hydrophobic upper surface 11 of the working film 10. This gap 12 is defined by the peripheral spacer 9. Here, the peripheral spacer 9 preferably is configured as a peripheral rim 9' that surrounds an area of the gap 12 and that is integrally formed with the body 2. Alternatively and as shown in FIG. 1, the peripheral spacer 9 is configured as a separate peripheral element 9" that surrounds the gap 12 and that is attached to the lower surface 4 of the body 2 that here is configured as a frame structure 2". As depicted, the working film 10 preferably is attached to the peripheral rim 9' of the plate-like structure 2'.

Preferably, and as large and numerous as necessary, the cartridge 1 comprises intermediate spacers 15 that are located within the area of the gap 12 and that are integrally formed with the plate-like structure 2'. These intermediate spacers 15 preferably have the same height as the peripheral rim 9' and preferably define the same gap dimension.

This cartridge 1 also comprises a number of piercing elements 13 that are located below piercable bottom structures 8 and that are configured to pierce the piercable bottom structures 8 for releasing reagents or samples 6,6' from the wells 5 into the gap 12. In the embodiment of the cartridge as depicted in FIG. 2, the piercing elements 13 are located within the area of the gap 12 and close to the peripheral rim 9'. The piercing elements 13 here are attached to the peripheral rim 9' and/or to the lower surface 4 of the body 2 of the plate-like structure 2'. Preferably, the piercing elements 13 are located below a well 5 or an intake recess and are configured to pierce at least the piercable bottom structure 8 when actuated by an actuating element 41 of a system 40 for liquid droplet manipulation. The actuating elements 41 preferably are guided in their movements by a guiding channel 45.

Preferably, the cartridge 1 comprises at least one optical fiber 21 for bringing light to a droplet 23 (here only indicated in dotted lines) in the gap 12 and/or for guiding light away from a droplet 23 in the gap 12. In FIG. 2, a so called top reading optical system is indicated by the optical fiber 21. With this optical system, excitation light (originating from a light source (not shown) can be directly brought into the droplet 23 with sample material in it. If the sample material comprises a fluorophor, this fluorophor will emit fluorescence that then is detected by the optical top reading system and a detector connected to the latter. Accordingly, the top reading system in the embodiment shown in FIG. 2 is configured to send excitation light to the sample and to receive and detect fluorescence emitted by the sample. Preferably the optical fiber 21 is integrated into the body 2 of the cartridge 1. As already shown in FIG. 1, the substrate 42 also comprises electrical lines that link the individual electrodes 44 with a central control unit 43 of the system 40.

Figure 3:
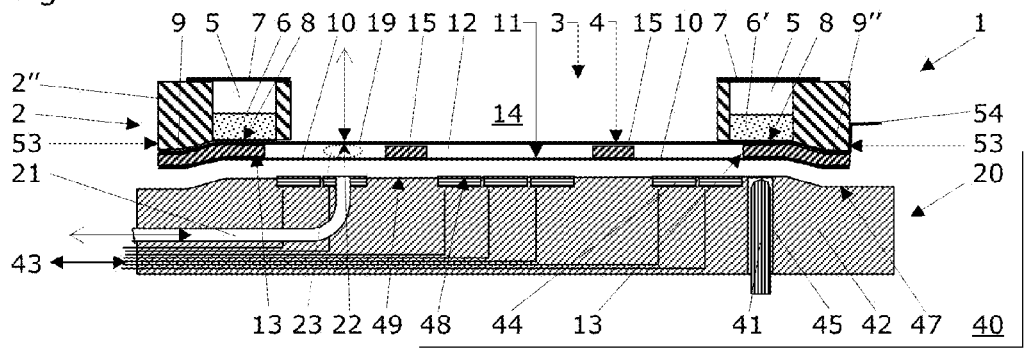
FIG. 3 a vertical cross-section through a frame structured cartridge according to a third related embodiment with a central opening across the body, with a number of wells and a working film contacted by a separate peripheral spacer; the cartridge is almost in contact with the electrode array of a system for liquid droplet manipulation.

FIG. 3 shows a vertical cross-section through a frame structured cartridge 1 according to a third related embodiment with a central opening 14 across the entire height of the body 2. The cartridge 1 comprises a number of wells 5 and a working film 10 contacted by a spacer 9 that is configured as a separate peripheral element 9". The cartridge 1 is almost in contact with the electrode array 20 of a system 40 for liquid droplet manipulation.

This cartridge 1 comprises a working film 10 for manipulating samples in liquid droplets with an electrode array 20 when the working film 10 of the cartridge 1 is placed on said electrode array 20. This cartridge 1 also comprises a body 2, which body 2 preferably comprises an essentially flat lower surface 4. According to the third related embodiment, the body 2 is configured as a frame structure 2" with a central opening 14 that extends across the entire height of the body 2. The body 2 comprises an upper surface 3, a lower surface 4, and a number of wells 5 configured to hold therein reagents 6 or samples 6'.

The lower surface 4 of the frame structure 2" of the body 2 is not completely flat: The body 2 comprises an outer part 53 that is extended downwards. Instead of having a completely flat spacer 9 in the form of a separate peripheral element 9", this embodiment comprises a separate peripheral element 9" that is downwards bent according to the lower surface of the body 2.

The substrate 42, which is adapted to this special lower surface of the cartridge 1, comprises a surface 49 which is offset to a surface level 48 of the electrodes 44 such that at least a part of the lower surface 4 of the body 2,2',2" or of the spacer 9 of the cartridge 1 to which the working film 10 is attached is movable beyond the surface level 48 of the electrodes 44 for stretching the working film 10 on the electrodes 44.

Preferably the material of the body 2 is of an inert plastic material that is impermeable to liquids and that does not take up or interfere with the liquids or samples contained in the wells 5. The same plastic materials for injection molding of the body 2 as for the frame structure 2" in FIG. 1 are also preferred for producing the frame structure 2" of this embodiment.

This cartridge 1 also comprises a flexibly deformable top structure 7 that is impermeable to liquids and that is configured to seal a top side of the wells 5. Preferably and as depicted, the flexibly deformable top structure 7 is configured as a flexible foil that corresponds to the flexible foil in FIG. 1.

This cartridge 1 also comprises a piercable bottom structure 8 that is impermeable to liquids and that is configured to seal a bottom side of the wells 5. Preferably and as depicted, the piercable bottom structure 8 is configured as a piercable cover layer 19. This cover layer 19 is configured as a piercable foil that is sealingly attached to the lower surface 4 of the frame structure 2" in a way that the cover layer 19 closes the gap 12 on a side opposite to the working film 10. Preferably, the lower surface of the cover layer 19 is essentially flush with the lower surface 4 of the frame structure 2".

Preferably the cover layer 19 is electrically conductive and is hydrophobic at least on a surface directed to the gap 12. The cover layer may also be chosen such that the material of the cover layer 19 is from an electrically conductive and hydrophobic material, e.g. PTFE. In this case of an electrically conductive cover layer 19, a cartridge 1 is preferred that comprises an electrical ground connection 54 which is connected to the cover layer 19 and which is attachable to a ground potential source of the system 40 for liquid droplet manipulation.

This cartridge 1 also comprises a working film 10 that is located below the lower surface 4 of the body 2,2". The working film 10 is impermeable to liquids and comprises a hydrophobic upper surface 11, on which the droplets are to be moved by electrowetting techniques. All embodiments of the working film 10 as well as the additional dielectric layer as described in connection with FIGS. 1 and 2 are also preferred for the cartridge depicted in FIG. 3.

This cartridge 1 also comprises a peripheral spacer 9 that is located below the lower surface 4 of the body 2,2',2" and that connects the working film 10 to the cover layer 19 and to the body 2,2',2". This cartridge 1 also comprises a gap 12 between the cover layer 19 and the hydrophobic upper surface 11 of the working film 10. This gap 12 is defined by the peripheral spacer 9. Here, the peripheral spacer 9 is configured as a separate peripheral element 9" that surrounds an area of the gap 12 (compare with FIG. 1). As depicted, the working film 10 preferably is attached to the separate peripheral element 9" of the frame structure 2".

Preferably, and as large and numerous as necessary, the cartridge 1 comprises intermediate spacers 15 that are located within the area of the gap 12 and that are attached to the lower surface of the cover layer 19 and/or to the hydrophobic upper surface 11 of the working film 10. These intermediate spacers 15 preferably have the same height as the separate peripheral element 9" and preferably define the same gap dimension.

This cartridge 1 also comprises a number of piercing elements 13 that are located below wells 5 or below an intake recess and that are configured to pierce the cover layer 19 for releasing reagents or samples 6,6' from the wells 5 or the intake recess into the gap 12. In the embodiment of the cartridge as depicted in FIG. 3, the piercing elements 13 are located similarly than shown in FIG. 1. Preferably, the piercing elements 13 are actuated by an actuating element 41 of a system 40 for liquid droplet manipulation. The actuating elements 41 preferably are guided in their movements by a guiding channel 45.

Here, the central opening 14 of the frame structure 2" is configured as a through hole from the upper surface 3 to the lower surface 4 of the body 2 e 2". Here, the cover layer 19 forms the substantially flat lower surface 4 of the body 2.

Preferably, the substrate 42 comprises at least one optical fiber 21 for bringing light to a droplet 23 (here only indicated in dotted lines) in the gap 12 and/or for guiding light away from a droplet 23 in the gap 12. In addition or alternately, it may be preferred to provide a window 22 in the cover layer 19 at a place that is opposite the gap 12 and in register with the entrance/exit opening of the optical fiber 21. In consequence, bottom reading (compare with FIG. 1) and/or top reading (compare with FIG. 2) is enabled by the third embodiment of FIG. 3. Preferably the optical fiber 21 is integrated into the substrate 42 of the electrode array 20 of the system 40 for the manipulation of droplets. This substrate also comprises electrical lines that electrically connect the individual electrodes 44 with a central control unit 43 of the system 40.

Figure 4:
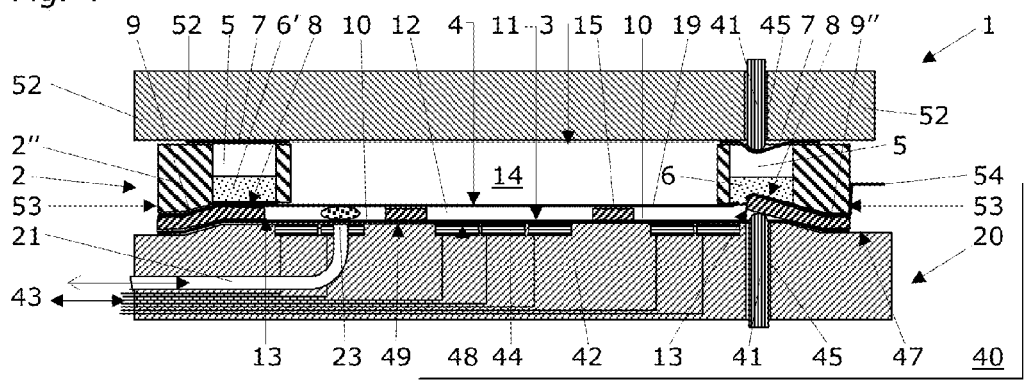
FIG. 4 a vertical cross-section through the frame structured cartridge according to the third related embodiment of FIG. 3; the cartridge is in contact with the electrode array of a system for liquid droplet manipulation, the piercable bottom structure of one well is open and some of its content is pressed into the gap between the working film and a cover layer.

FIG. 4 shows a vertical cross-section through the frame structured cartridge 1 according to the third related embodiment of FIG. 3. The cartridge 1 is in contact with the electrode array 20 of a system 40 for liquid droplet manipulation. The piercable bottom structure in the form of a cover layer 19 is opened for one well 5 and some of its content is pressed into the gap 12 between the working film 10 and the cover layer 19.

Like the substrate 42 in FIG. 3, the substrate 42 here comprises an abutment surface 47 which is offset to a surface level 48 of the electrodes 44 such that a separate peripheral element 9″ of the cartridge 1 to which the working film 10 is attached, is movable beyond the surface level 48 of the electrodes 44 for additionally stretching the working film 10 on the electrodes 44.

In this preferred embodiment of a system 40 for liquid droplet manipulation, a clamping mechanism 52 presses the cartridge 1 and its working film 10 onto the surface 48 of the electrodes 44 and onto the surface 49 of the substrate 42.

Figure 5:
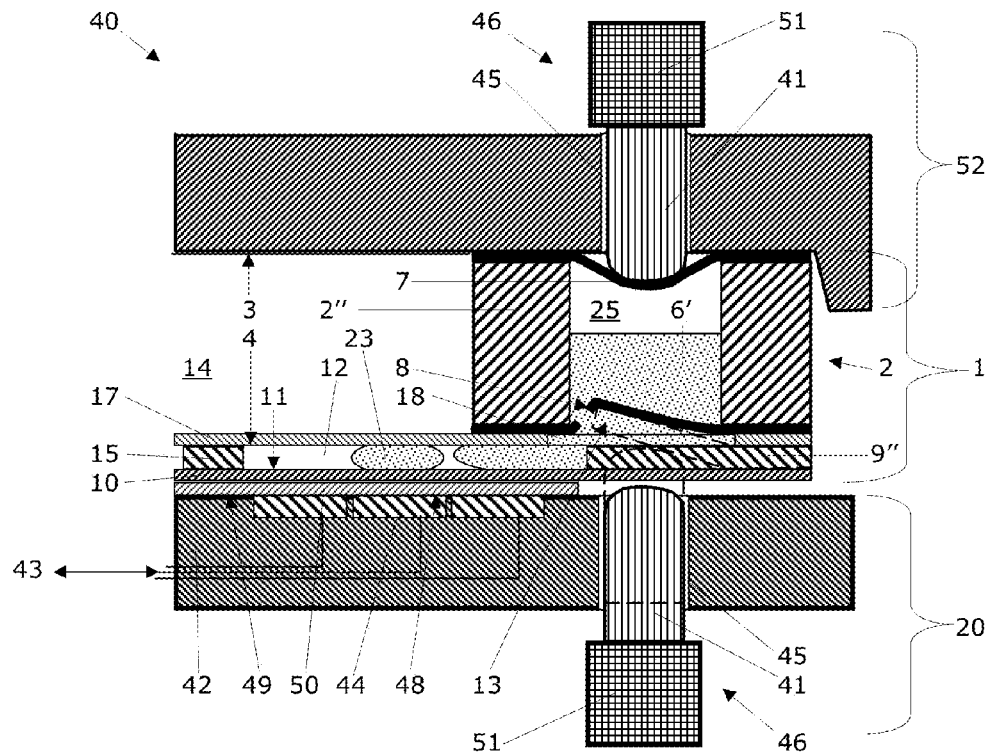
FIG. 5 a vertical cross-section through a frame structured cartridge according to a fourth related embodiment with a central opening across the body, with a number of wells and a working film contacted by a separate peripheral spacer; the cartridge is in contact with the electrode array of a system for liquid droplet manipulation; the piercable bottom structure of one well is open and some of its content is pressed into the gap between the working film and a cover layer that is configured as a rigid cover here.

FIG. 5 shows a vertical cross-section through a frame structured cartridge 1 according to a fourth related embodiment with a central opening 14 across the body 2, with a number of wells 5 and a working film 10 contacted by a separate peripheral spacer element 9‴. The cartridge 1 is in contact with the electrode array 20 of a system 40 for liquid droplet manipulation. The piercable bottom structure 8 of one well (the intake recess 25) is opened and some of its content is pressed into the gap 12 between the working film 10 and a cover layer 19 that is configured as a rigid cover 17 here. Rigidity is depending on the required thickness of the layer. The material for this rigid cover preferably is Mylar®, a transparent, flexible polyester foil on the basis of polyethylene terephthalat from DuPont. The rigid cover 17 may be coated on its underside with a layer of indium tin oxide (ITO) in order to provide the rigid cover 17 with an electrically conductive layer that can be connected to a ground potential source of the system 40 for liquid droplet manipulation. This FIG. 5 also depicts a system 40 for liquid droplet manipulation that comprises a cartridge 1 and an electrode array 20.

This cartridge 1 comprises a working film 10 for manipulating samples in liquid droplets 23 with an electrode array 20 when the working film 10 of the cartridge 1 is placed on said electrode array 20. This cartridge 1 also comprises a body 2, which body 2 preferably comprises an essentially flat lower surface 4, which is built by rigid cover 17 here. According to the fourth related embodiment, the body 2 is configured as a frame structure 2″ with a central opening 14 that extends across the entire height of the body 2. The body 2 comprises an upper surface 3, a lower surface 4, and a number of wells 5 and intake recesses 25 configured to hold therein reagents 6 or samples 6′.

Preferably the material of the body 2 is of an inert plastic material that is impermeable to liquids and that does not take up or interfere with the liquids or samples contained in the wells 5. The same plastic materials for injection molding of the body 2 as for the frame structure 2″ in FIGS. 1, 3, and 4 are also preferred for producing the frame structure 2″ of this embodiment.

This cartridge 1 also comprises a flexibly deformable top structure 7 that is impermeable to liquids and that is configured to seal a top side of the wells 5. Preferably an as depicted, the flexibly deformable top structure 7 is configured as a flexible foil that corresponds to the flexible foil in the FIGS. 1, 3, and 4.

This cartridge 1 also comprises a piercable bottom structure 8 that is impermeable to liquids and that is configured to seal a bottom side of the wells 5 and intake recesses 25. Preferably and as depicted, the piercable bottom structure 8 is configured as a piercable foil that is sealingly attached (e.g. by welding) to the lower surface 4 of the body 2. This piercable foil preferably is made of an elastomeric material, such as a rubber or a thermoplastic elastomer (TPE) membrane. Alternatively, the piercable bottom structure 8 is configured as a piercable bottom portion of the body 2 that is integrated in the plate-like structure 2′ (compare FIG. 1). In that case, the body material preferably is TPE.

In order to enable the piercing elements 13 for piercing the piercable bottom structure 8, the rigid cover 17 comprises cover holes 18, through which the piercing elements 13 easily reach the piercable foil. Preferably, the working film 10 is flexible so that no leaking out of liquids from the gap 12 has to be expected. All embodiments of the working film 10 as well as the additional dielectric layer as described in connection with the FIGS. 1 to 4 are also preferred for the cartridge depicted in FIG. 5.

The substrate 42, which is adapted to this flat lower surface of the cartridge 1, comprises a surface 49 which is flush with a surface level 48 of the electrodes 44 such that the working film 10 is stretched on the electrodes 44. An electrically insulating film, layer or cover 50 is applied to the surface 48 of the electrodes 44 and to the surface 49 of the substrate 42. This electrically insulating film, layer or cover 50 preferably is a dielectric layer that irremovably coats the electrodes 44 and substrate 42 of the system 40 for liquid droplet manipulation. It is however also preferred to provide an additional dielectric layer as a removable electrically insulating layer or cover 50 that can be replaced when needed.

The spacers 9,15 and piercing elements 13 of this cartridge 1 correspond with the spacers 9,15 and piercing elements 13 in FIG. 1 and define a gap 12 between the rigid cover 17 and the hydrophobic upper surface 11 of the working film 10. Preferably, the piercing elements 13 are actuated by an actuating element 41 of a system 40 for liquid droplet manipulation. The actuating elements 41 preferably are guided in their movements by a guiding channel 45. As depicted, the rigid cover 17 has essentially the same extension as the frame structure 2″ and comprises a number of holes 18 located below the wells 5. The holes 18 have a size and shape sufficient to allow bended piercing elements 13 to abut and pierce a respective piercable bottom structure 8 of a well 5.

In an alternative embodiment, the cartridge 1 comprises a rigid cover 17 and a cover layer 19 (the latter replacing the piercable foil as a piercable bottom structure 8). The rigid cover 17 and the cover layer 19 are attached to the frame structure 2″ in a way that the rigid cover 17 closes the gap 12 on a side opposite to the working film 10, a lower surface of the rigid cover 17 being essentially flush with the lower surface 4 of the frame structure 2". The cover layer 19 (not shown in FIG. 5) preferably is placed between the rigid cover 17 and the lower surface 4 of the body 2.

Preferably, the actuating elements 41 are configured as plungers that are slidingly movable in guiding channels 45 and that are agitated by an agitation mechanism 46. It also preferred that the agitation mechanism 46 for agitating the actuating elements 41 is configured as one of a wax pump bladder, a solenoid driven or clamping mechanism driven lever 51. It is further preferred that the agitation mechanism 46 for agitating the actuating elements 41 is configured as a clamping mechanism driven lever 51 and that the clamping mechanism 52 being hand driven and configured to press the body 2,2',2" of a cartridge 1 onto the substrate 42 and electrode array 20 of the system 40 for liquid droplet manipulation. Alternately, the clamping mechanism 52 is motor driven.

Figure 6:
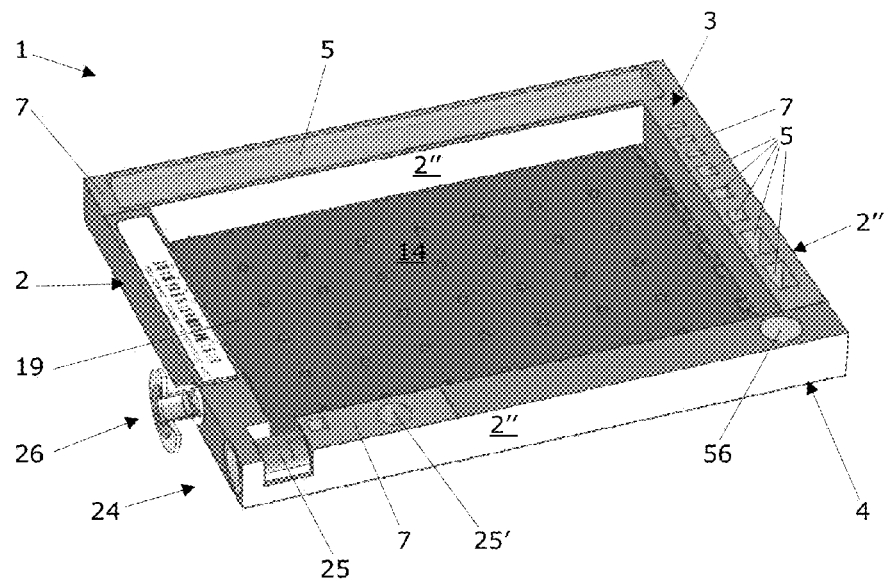
FIG. 6 a 3D top view of a frame-like cartridge according to the third or fourth related embodiment with an intake device in a passive position.

The FIG. 6 shows a 3D top view of a frame-like cartridge 1 according to the third or fourth related embodiment with an intake device 26 in a passive position. The body 2,2" of the cartridge 1 preferably comprises a specimen intake 24 that comprises an intake recess 25 and an intake device 26, the intake device 26 being at least partially positionable in an active position in the intake recess 25. This specimen intake 24 is configured to introduce a buccal swab head 55 or other solid material comprising a sample to investigate.

The FIG. 6 also shows in the cross bar of the body 2 on the right side of the cartridge a number of wells 5 of different size for pre-depositing reagents and other liquids like wash fluids etc. In the longitudinal bar on the rear of the body 2 is shown a very long well 5, which is configured to take up pre-deposited oil. The oil can be used for filling the gap 12 prior to enter sample drops into the gap 12. Complete filling of the gap 12 with an oil that is not miscible with the samples that normally are contained in a hydrous droplet and that is inert (e.g. silicon oil) is optional. As can be seen from FIG. 6, the size of the wells 5 can be chosen according to the actual need for carrying out particular assays. A flexibly deformable top structure 7 that is configured as foil impermeable to liquids seals the top side of the wells 5. The flexible foil is sealingly attached to the upper surface 3 of the frame structure 2" by laser welding for example.

In the longitudinal bar on the front of the body 2 is shown an alternative intake recess 25' for introducing a sample of body fluid (like blood, saliva, etc.). This alternative intake recess 25' preferably is sealed on its top side by a foil that is impermable to liquids, but that is also piercable with a needle of a medical syringe and that is flexible for being pushed by a piston-like actuating element for bringing the sample into the gap 12 of the cartridge 1 after the piercable bottom structure 8 has been pierced from the bottom side of the cartridge 1 with a piercing element 13. The material for the foil that seals the top side of the alternative intake recess 25' preferably is rubber.

In the right front corner of the cartridge, a frit 56 that is located in a channel which reaches down to the lower surface 4 of the body 2 and that preferably is combined with a semi-permeable membrane (not shown) is depicted. This frit 56 and the channel serves as a vent for the gap 12 as soon as a piercable bottom structure 8 that sealingly closes the bottom of the channel has been pierced from the bottom side of the cartridge 1 with a piercing element 13.

A large number of intermediate spacers 15 can be seen through the optically transparent rigid cover 17 or cover layer 19. Although all intermediate spacers 15 drawn here are of equal size and round shape, and although these intermediate spacers 15 are distributed over the gap 12 at equal distances, the shape, size and distribution of these intermediate spacers 15 can be chosen as needed, if the intended electrowetting movements of the droplets 23 are not compromised.

Figure 7:
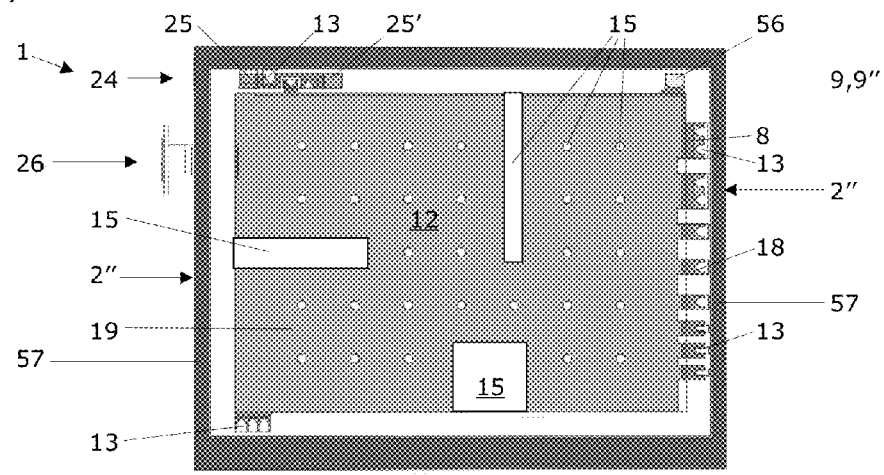
FIG. 7 a bottom view of a frame-like cartridge according to the third or fourth related embodiment of FIG. 6 with an intake device in a passive position.

The FIG. 7 shows a bottom view of a frame-like cartridge 1 according to the third or fourth related embodiment of FIG. 6 with an intake device 26 in a passive position. The working film 10 has been removed here so that the spacer 9 configured as a peripheral element 9''' is visible. Deviating from the cross sections shown in the FIGS. 4 and 5, where the peripheral element 9''' extends to the outer borders of the cartridge 1, the peripheral element 9''' here is bordered by a downward extension 57 of the body 2. This downward extension 57 of the body 2 in combination with the lower surface of the working film 10 (that is attached to the peripheral element 9''') preferably provides the entire cartridge with a flat lower surface. Alternately, the downward extension 57 of the body 2 is flush with the peripheral element 9''' and the working film 10 is attached to the working film 10 and as well to the downward extension 57 of the body 2.

As being parts of the peripheral element 9''', many piercing elements 13 can be seen here. Depending from the size of the well 5 above, the size and number of the piercing elements 13 can vary: i.e. for the oil containing well, three piercing elements 13 are depicted (see lower left); for the two largest wells that contain reagents, two piercing elements 13 are depicted (see upper right); and for the smaller wells containing reagents, only one piercing element 13 are depicted (see lower right). The piercing element 13 that is configured to pierce the piercable bottom structure 8 below the intake recess 25 is shown on the left side of the top bar of the body 2. The shown number, size and shape of these piercing elements 13 is only exemplary here and can vary according to actual needs.

As already noted with respect to FIG. 6, the shape, size and distribution of the intermediate spacers 15 can be chosen as needed, if the intended electrowetting movements of the droplets 23 are not compromised. Here are three exemplary intermediate spacers 15 shown that clearly deviate from the ones of FIG. 6.

The FIG. 8 shows detailed 3D views of the specimen intake 24 of a frame-like cartridge 1 according to the third or fourth related embodiment.

Figure 8A:
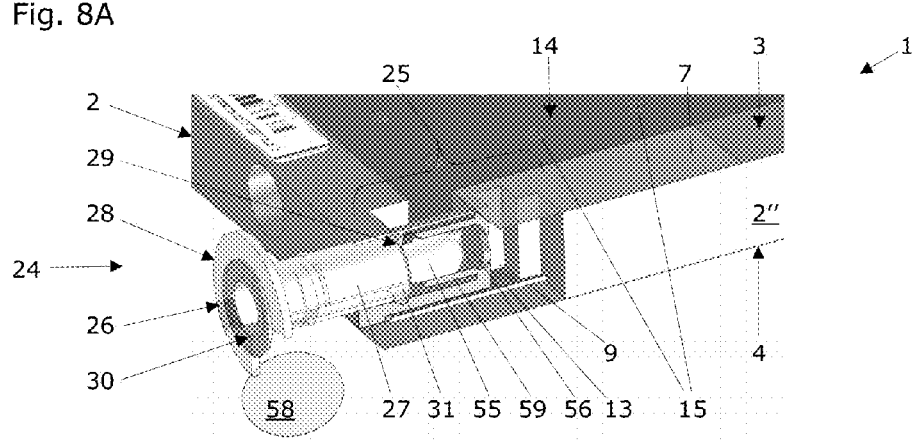
FIG. 8A a semi cross-section of the specimen intake of the frame-like cartridge with a partially inserted intake device in the active position.

FIG. 8A shows a semi cross-section of the specimen intake 24 of the frame-like cartridge with a partially inserted intake device 26 in the active position. The intake device 26 preferably comprises a cylinder tube 27 with a first end 28 and with a second end 29, a plunger 30 that is insertable on the first tube end 28 and that is movable in the cylinder tube 27, and a sealing foil 31 that sealingly closes the second end 29 of the cylinder tube 27. In the space inside the cylinder tube 27 and between the plunger 30 and the sealing foil 31, a pre-deposit of lysis buffer is provided. A frit 56 is also visible. This frit 56 separates the part of the intake recess 25 (the outer chamber) in which the sample carrier, such as a buccal swab head 55, is placed for lysis of cellular material and the part of the intake recess 25 (the inner chamber) where the lysate is pressed into after the lysis. The intake device 26 obviously has been moved from the passive position (see FIGS. 6 and 7) to the active position, where the intake recess 25 of the cartridge 1 is located. A flexibly deformable top structure 7 that is configured as a foil and that is impermeable to liquids seals the top side of intake recess 25. The flexible foil is sealingly attached to the upper surface 3 of the frame structure 2" by laser welding for example.

Figure 8B:
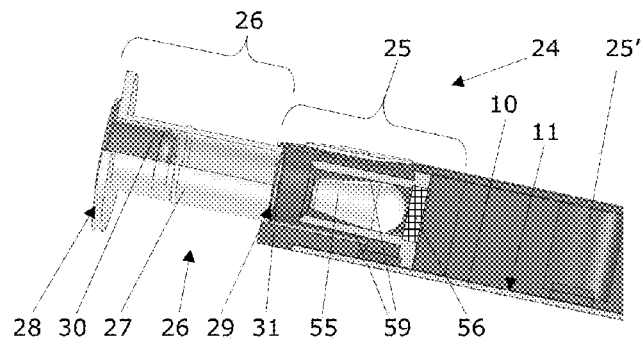
FIG. 8B a semi cross-section of the specimen intake of the frame-like cartridge and of the partially inserted intake device in the active position.

FIG. 8B shows a semi cross-section of the specimen intake 24 of the frame-like cartridge 1 and of the partially inserted intake device 26 in the active position. The situation depicted here is the following:

1. A sample was taken with a buccal swab and the specimen (the buccal swab head 55 with the adhering sample) was introduced into the outer chamber of the intake recess 25 after peeling off a seal 58 that prevents the intake recess 25 from contamination before use (see FIG. 8A).
2. The intake device 26 is now pushed into the intake recess 25. The outer circumference of the cylinder tube 27 is sealing gliding in the cylinder-like outer chamber of the intake recess 25.

The next steps of introducing a sample into the gap 12 of the cartridge 1 will be:

3. The intake device 26 is pushed further into the intake recess 25 until a piercing structure 59 in the outer chamber of the intake recess 25 is piercing the sealing foil 31 that sealingly closes the second end 29 of the cylinder tube 27.
4. The lysis buffer originally contained in the cylinder tube 27 is entering the outer chamber of the intake recess 25 and the intake device 26 is pushed further into the intake recess 25 in order to push out air through the frit 56 between the outer and the inner chamber of the intake recess 25.
5. Lysis of cellular material that adheres to the swab head 55 is performed. During lysis, the temperature preferably is enhanced in the intake recess 25. A heater in the substrate 42 of the system 40 for manipulating droplets (or alternately in the cartridge 1) is preferably used for raising the temperature inside the intake recess 25 to the required values.
6. After lysis, the cylinder tube 27 of the intake device 26 is completely pushed into the outer chamber of the intake recess 25. When doing this, a large portion of the lysate is pressed through the frit 56 and enters the inner chamber of the intake recess 25.
7. If required, the gap 12 of the cartridge is first filled with oil. The piercable bottom structure 8 below the inner chamber of the intake recess 25 then is pierced by pushing a piercing element 13 against the piercable bottom structure 8 with the help of a plunger 41.
8. The flexibly deformable top structure 7 that sealingly closes the top of the inner chamber of the intake recess 25 is pushed inwards with the help of a plunger 41 and by reducing the internal volume of the inner chamber of the intake recess 25 some of the lysate is release to the gap 12.

Figure 9:
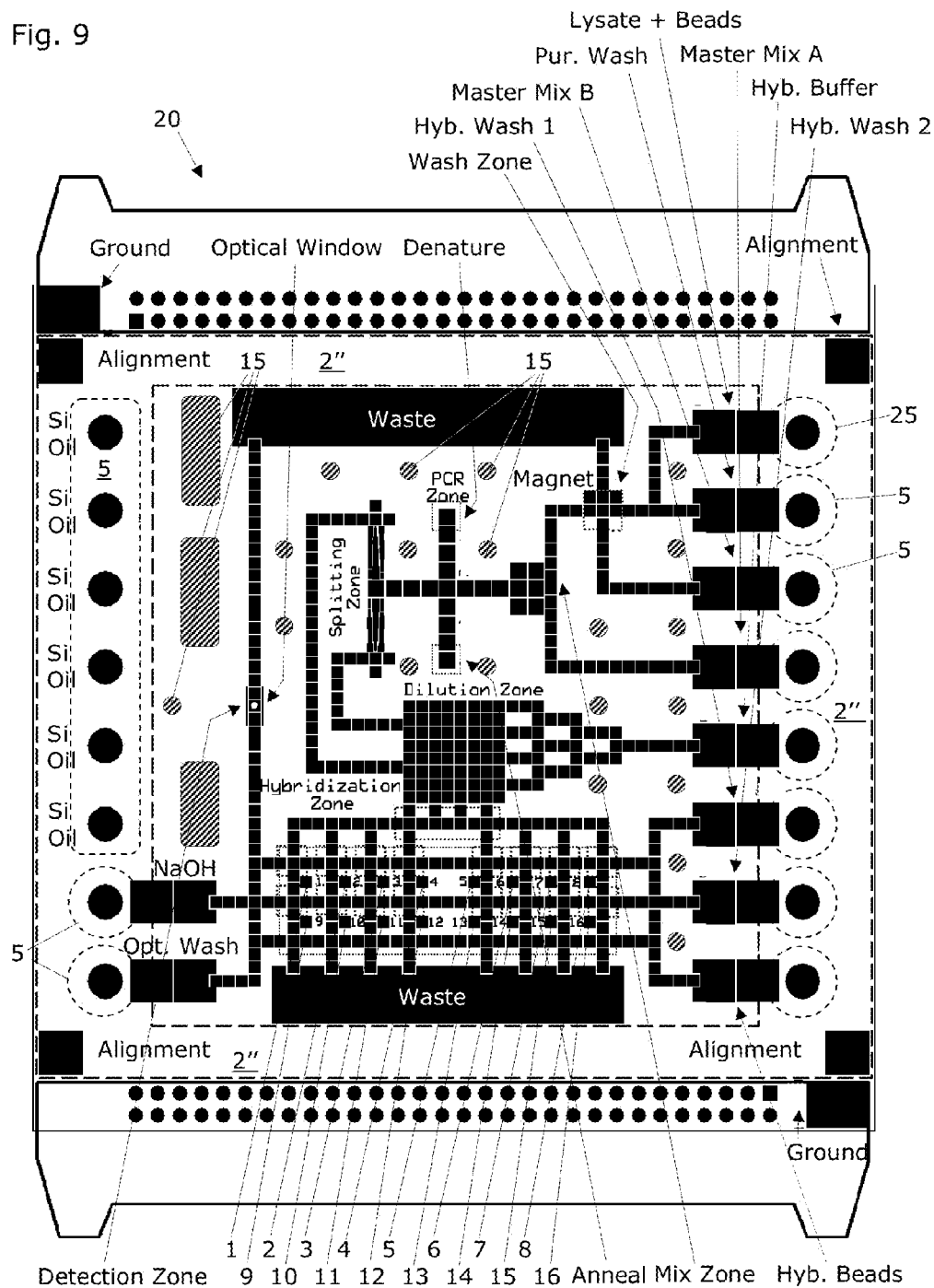
FIG. 9 a top view of an electrode layout of a system for liquid droplet manipulation that is configured for receiving a frame-like cartridge according to the third or fourth related embodiment, the layout being particularly configured to match for lysis of cellular material, for extraction and PCR amplification of DNA fragments, for hybridization experiments for genotyping, and for optical detection.

The FIG. 9 shows a top view of an electrode layout or printed circuit board (PCB) of a system 40 for liquid droplet manipulation. This particular electrode array 20 of the system 40 is configured for receiving a frame-like cartridge 1 according to the third or fourth related embodiment. Accordingly, the shape of the cartridge 1 with its central opening 14 is indicated in longer dashed lines here. The shape of the wells 5 and intake recess 25 is indicated in shorter dashed lines.

This electrode array 20 is particularly configured to match for the lysis of cellular material, for the extraction and PCR amplification of DNA fragments, for the hybridization experiments for genotyping, and for the optical detection. Four alignment marks in the corners of the electrode array facilitate alignment of the array.

Starting on the left (if required), the entire gap 12 is flooded with silicon (Si) oil. Then (see top right), from the intake recess 25 lysate (with or without beads) is entering the gap 12. Directly at the entrance to the gap 12, where the piercable bottom structure 8 of the corresponding well 5 is pierced, preferably is located a first large electrode that is accompanied by a second large electrode. The second large electrode in each case has a cut out, where the first of a row of individual electrodes 44 is placed.

These two large electrodes mark the area, where a portion of the liquid from the respective well 5 or intake recess 25 is deposited after piercing the piercable bottom structure 8 from below and pressing the flexible deformable top structure 7 from the top. From this portion of liquid, single small droplets of a typical volume of 0.1 to 5 µl are separated. The wells adjacent to the intake recess 25 (from top to bottom of the FIG. 9) are assigned to pure wash liquid, master mix B, master mix A, hybridization buffer, hybridization wash solution 1, hybridization wash solution 2, and beads for hybridization.

A droplet of lysate and of pure wash liquid are moved by electrowetting to the wash zone where these droplets are mixed and washed and the magnetic beads and attached non-important sample parts are moved to a first waste zone, which is provided by a very large electrode. At the wash zone and at the adjacent mix zone, master mix portions A and/or B can be added to the sample droplet. Then, a droplet is moved to the zone for polymerase chain reaction (PCR) where the nucleic acids contained in the sample droplet are amplified according to techniques known per se. The PCR zone comprises at least two heater zones with a different temperature (e.g. 35° C. and 95° C.) for annealing and separating the strands of the nucleic acids.

Following PCR, a single ample drop with amplified nucleic acids is split into two smaller droplets at a splitting zone that preferably is characterized by the particular shape and arrangement of electrodes as depicted. In the central dilution zone, both of these two sample droplets are individually diluted with hybridization buffer and up to eight identical droplets are produced from each one of these two split sample droplets.

At the hybridization spots 1-4 and 9-12 or 5-8 and 13-16, the twice eight sample droplets are subjected to hybridization according to techniques known per se. Following hybridization, the added, non-hybridized material is thoroughly washed away and discarded in a nearby second waste zone (which again is provided by a very large electrode).

Each one of the sixteen sample droplets is then individually moved (with electrowetting again) to a detection zone, where (using bottom reading, top reading, or a mixture or combination of both) the hybridized samples are optically analyzed.

Following analysis of the samples in the sample droplets that are still in the gap 12 of the cartridge 1, the samples are discarded to the first waste zone and the "electrowetting path" provided by a large row of individual electrodes 44 is washed and cleaned a sodium hydroxide solution (NaOH) and optionally with a special wash solution.

When all the experiments and measurements are completed, the cartridge 1 (together with the samples and the waste in it) is safely discarded so that nobody of the laboratory personnel is endangered by its contents. Then, the next cartridge 1 is pressed onto the electrode array 20 and the next experiments can be performed.

In the FIG. 9 (see on top and on the bottom of the Figure), a large number of contact points are seen. Individual electric lines contact each electrode with one of these contact points. In addition, heaters located in the substrate 42 of the system 40 are also connected to some of these contact points. All contact points are connected with the central control unit 43 which controls all necessary activations of e.g. heaters, plungers 41 etc. and of all electrical potentials of the electrodes that are required. On each side of the electrode array is also provided a separate contact point for contacting with ground potential source of the central control unit 43.

Preferably, the system 40 for liquid droplet manipulation comprises a substrate 42 with an electrode array 20 and a central control unit 43 for controlling the selection of individual electrodes 44 of the electrode array 43 and for providing the electrodes 44 with individual voltage pulses for manipulating liquid droplets 23 by electrowetting. The preferred system 40 is configured to receive on top of the electrodes 44 the working film 10 of a cartridge 1 according to the present invention. The system 40 can be a stand alone and immobile unit, on which a number of operators is working with cartridges 1 that they bring along. The system 40 thus may comprise a number of substrates 42 and a number of electrode arrays 20, so that a number of cartridges 1 can be worked on simultaneously and/or parallel. The number of substrates 42, electrode arrays 20, and cartridges 1 may be 1 or any number between e.g. 1 and 100 or even more; this number e.g. being limited by the working capacity of the central control unit 43. Alternatively, the system 40 can be can be implemented as a hand held which only comprises and is able to work with a single cartridge 1. Every person of skill will understand that intermediate solutions that are situated in-between the two extremes just mentioned will also operate and work within the gist of the present invention.

In a preferred fifth embodiment, a cartridge 1 according to the present invention comprises a working film and at least one piercing element 13, for manipulating samples in liquid droplets with an electrode array 20 when the working film 10 of the cartridge 1 is placed on said electrode array 20. In this embodiment, the cartridge 1 comprises a body 2,2',2" that comprises an upper surface 3, a lower surface 4, and a number of wells 5 which are configured to hold therein reagents 6 or samples 6'. Each well 5 comprises a top opening 72, and a bottom opening 73 for releasing a liquid from the well 5. The cartridge further comprises a piercable bottom structure 8 which is impermeable to liquids and which is configured to seal at least one of the bottom openings 73 of the wells 5. A working film 10 is located below the lower surface 4 of the body 2,2',2", is impermeable to liquids, and comprises a hydrophobic upper surface 11. The cartridge 1 comprises a peripheral spacer 9 which is located below the lower surface 4 of the body 2,2',2" and which connects the working film 10 to the body 2,2',2"; and a gap 12 between the lower surface 4 of the body 2,2',2" and the hydrophobic upper surface 11 of the working film 10. The gap 12 is defined by the peripheral spacer 9.

In this fifth embodiment, the cartridge 1 further comprises at least one top piercing system 60, each located within at least one of the wells 5 for releasing a reagent or sample 6,6' from said at least one well 5 into the gap 12. Each top piercing system 60 comprises a piston 61 and a piercing element 13. The piston 61 is configured to be movable within said well 5 while providing a seal between the piston 61 and the inner wall of the well 5. The piercing element 13 is configured as a thorn 63 located at a front side 74 of the piston 61 and is configured to pierce the piercable bottom structure 8 for releasing a reagent or sample 6,6' from said at least one well 5 into the gap 12 upon moving the piston 61 within the well 5 toward its bottom opening 73.

The fifth embodiment of a cartridge 1 according to the present invention is discussed in more detail below. Generally, the embodiments and materials e.g. of the body 2,2',2", the spacer 9,15, the rigid cover 17 or the cover layer 19, the gap, the working film 10, and also of the electrode array 20, the substrate 42 and the central control unit 43, as discussed previously, may be applied also for this fifth embodiment according to the present invention. For a better understanding, materials, material characteristics and dimensions which are suitable for the respective components of a cartridge 1 and system according to the present invention in the fifth embodiment are summarized in Table 1.

FIG. 10 shows a vertical cross section through a frame structured cartridge 1 according to the fifth embodiment comprising a top piercing system 60 according to the present invention. The body 2 of the cartridge 1 is shown to be configured as a frame structure 2" with a central opening 14, which is closed by a bottom portion 16. Alternatively, the central opening 14 may extend across the entire height of the body 2,2", as shown in the FIG. 3; or the body 2 may be accomplished as a plate-like structure 2', as it is exemplarily shown in the FIGS. 2, 13 and 14. The cartridge 1 is in contact with an electrode array 20 of a system 40 for liquid droplet manipulation. The body 2,2',2" comprises a number of wells 5, though only one specific well 5 is depicted here. Each well 5 comprises a top opening 72 at the upper surface 3 of the body 2,2',2", a bottom opening 73 at the lower surface 4 of the body 2,2',2", and an inner bottom 76.

Preferably, the material of the body 2,2',2" is of an inert plastic material that is impermeable to liquids and that does not take up or interfere with the liquids or samples 6,6' contained in the wells 5, as discussed before and in Table 1. Possible production methods are injection molding, cutting and/or punching. In a particular preferred embodiment, the body 2,2',2" is made of polypropylene (PP).

The cartridge 1 comprises at least one piercing element 13 that is configured as a thorn 63 located at a front side 74 of a piston 61. The piston 61 with the thorn 63 are located within at least one of the wells 5 of the cartridge, forming a top piercing system 60 which enables the piercing of a piercable bottom structure 8 from its top side. The piston 61 is movable within said well 5 while providing a seal between the piston 61 and the inner wall of the well 5. The piercing element 13 is configured to pierce the piercable bottom structure 8 for releasing a reagent or sample 6,6' from said at least one well 5 into the gap 12 upon moving the piston 61 within the well 5 toward its bottom opening 73.

The cartridge 1 further comprises a working film 10 for manipulating samples with the electrode array 20 when the working film 10 of the cartridge 1 is placed on said electrode array 20. This working film 10 is impermeable to liquids and comprises a hydrophobic upper surface 11, on which the droplets 23 are moved by electrowetting techniques. The working film 10 shown in FIG. 10 is configured as a monolayer of hydrophobic material that is also electrically insulating. Alternatively, the working film 10 may be configured as a hydrophobic monolayer of a material which is not electrically insulating. In this case, an additional dielectric layer, i.e. an electrically insulating layer 50 has to be placed between the working film 10 of the cartridge and the electrode array 20, as it is described above and as it is shown in FIG. 14. In a further alternative embodiment, the working film 10 is configured as a monolayer of electrically non-conductive material, the upper surface 11 of the working film 10 being treated to be hydrophobic. Principally, all embodiments of the working film 10 as described in connection with the FIGS. 1 to 5 are possible alternative embodiments for a working film 10 of the cartridge 1 comprising the top piercing system 60 described here.

The cartridge 1 also comprises a peripheral spacer 9 that is located below the lower surface of the body 2,2',2" and that connects the working film 10 to the body 2,2',2". The cartridge also comprises a gap 12 between the lower surface 4 of the body 2,2',2" and the hydrophobic upper surface of the working film 10. This gap 12 is defined by the peripheral spacer 9. In the embodiment of the cartridge 1 shown in FIG. 10, the peripheral spacer 9 is attached to the lower surface 4 of the piercable bottom structure 8, i.e. to the piercable foil 79.

The cartridge may further comprise one or more intermediate spacers 15 that are configured as separate elements located within the area of the gap 12 and attached to the lower surface 4 of the piercable bottom structure 8 or piercable foil 79, as discussed before. Intermediate spacers 15 preferably have the same height as the peripheral spacer 9 and preferably define the same gap dimension.

It may be appropriate dividing or partitioning the gap 12 of a particular cartridge 1 into two or more partial gaps (not shown); such dividing may be accomplished by having at least one intermediate spacer 15 reaching from the peripheral spacer 9 of one side of the cartridge to the peripheral spacer 9 of another side of the cartridge. Such dividing may also be accomplished by having two or more peripheral spacers 9, each of which surrounding only a part of the piercable foil 79 and thus only a part of the (instead of the entire) foot print of the cartridge 1.

In the cartridge shown in FIG. 10, the piercable bottom structure 8 is configured as a piercable foil 79 that may be sealingly attached to the lower surface 4 of the body 2,2". This piercable foil 79 is impermeable to liquids, has low moisture trans-mission and is configured to seal at least one of the bottom openings 73 of the wells 5 of the cartridge 1 which preferably comprise (in each case) a top piercing system 60 according to the present invention. The piercable foil 79 is sized to seal at least one selected well 5 of the cartridge, which comprises a top piercing system 60. Alternatively, the piercable foil 79 may be sized to seal two or more wells 5 of the cartridge, independently, whether these wells 5 comprise a top piercing systems 60, whether they remain empty or whether an alternative piercing system is provided e.g. for piercing the piercable foil 79 from below the body 2. In a preferred embodiment, the piercable foil 79 is sized to cover the complete lower surface 4 of the body 2,2',2", sealing the bottom openings 73 of all wells 5 of the body 2,2',2".

The piercable foil 79 shown in FIG. 10 is configured as a piercable cover layer 79' which closes the gap 12 on a side opposite to the working film 10. When configured as a piercable cover layer 79', the surface of the piercable foil 79 which is oriented to the gap 12 preferably is hydrophobic to facilitate the manipulation of a liquid droplet with the electrode array 20. Exemplarily, such a piercable foil 79 may be an aluminum foil which is coated with a hydrophobic polymer such as Teflon® on its surface oriented to the gap 12, and which is further coated with a sealing polymer such as PP (when the body 2,2',2" is also made of PP) for heat sealing the piercable foil 79 to the body 2,2',2".

Figure 13:
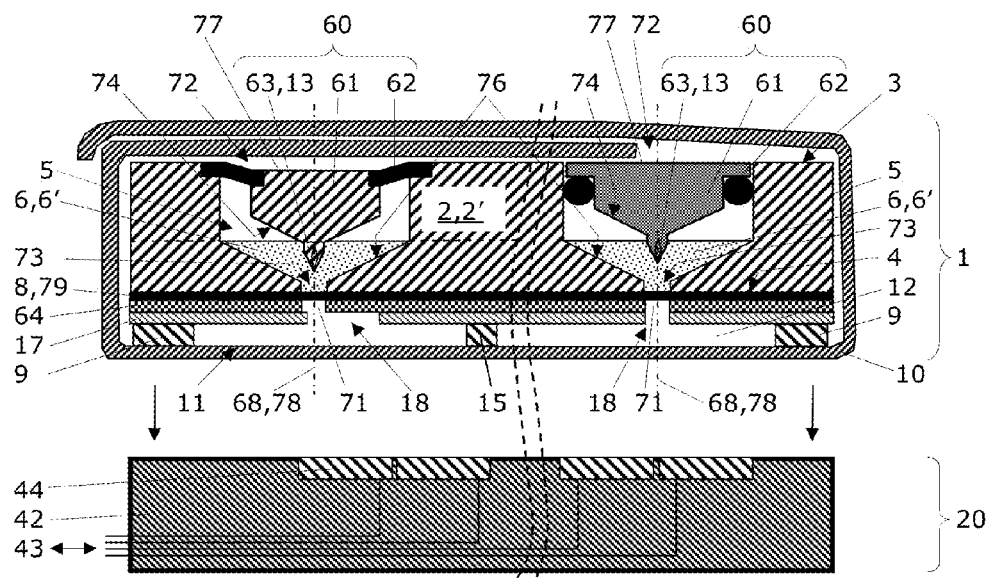
Figure 14:
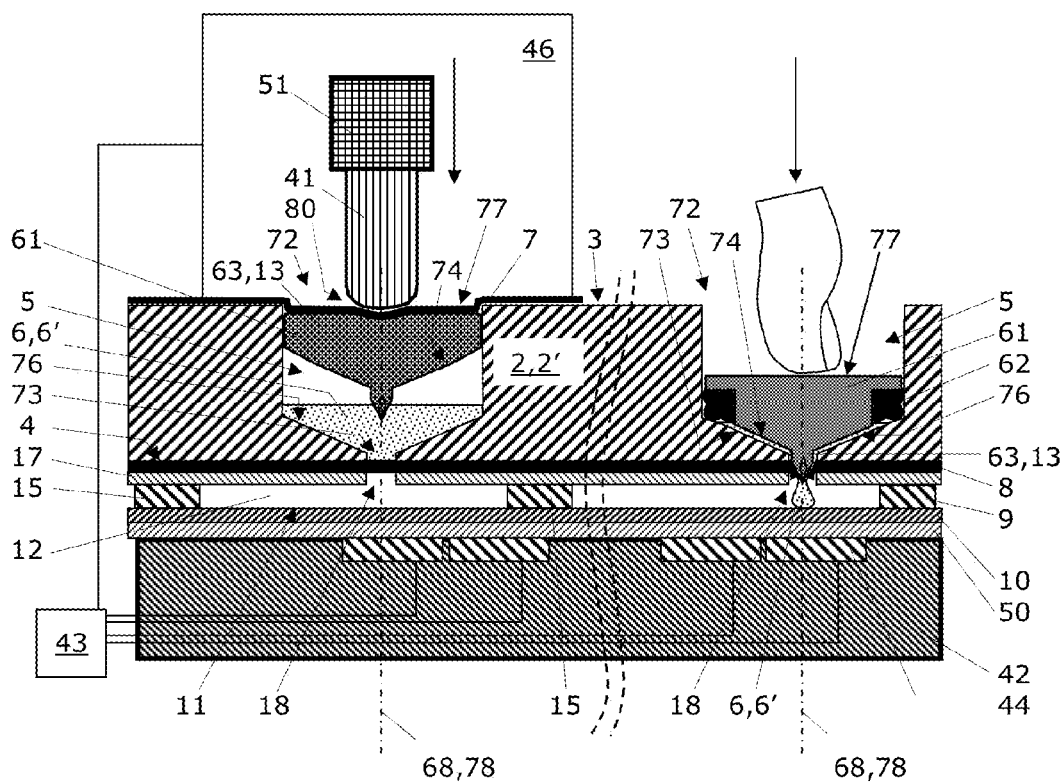
FIG. 14 a vertical cross section through a plate-like structured cartridge, with a two-layered working film and two exemplarily shown wells, each having a top piercing system; the cartridge comprising a piercable bottom foil and a cover layer which additionally provides a relief opening for the thorn.

When the piercable foil 79 is not configured as a piercable cover layer 79', e.g. when made of a material which is not hydrophobic, or when the body 2 is configured as a frame structure 2" with a central opening that extends across the entire height of the body 2,2" so that additional stabilization is desirable, the cartridge 1 might comprise an additional rigid cover 17 or cover layer 19 which provides the hydrophobic surface, as exemplarily shown in the FIGS. 13 and 14.

The piercable bottom structure 8 is preferably configured as a piercable foil 79 that is sealingly attached (e.g. by welding or gluing) to the lower surface 4 of the body 2,2',2'. This piercable foil 79 preferably extends over the entire lower surface 4 of the body 2,2',2". Alternatively, the piercable foil 79 essentially covers the area of the lower surface 4 below a well 5 comprising the top piercing system 60.

The at least one top piercing system 60 is located within the well 5 as shown in FIG. 10. The top piercing system 60 is accomplished to pierce the piercable bottom structure 8 of the cartridge 1 for generating a through hole and a fluid path for releasing a reagent or sample 6,6' from that specific well 5 into the gap 12. Though only one well 5 having the top piercing system 60 is shown, further wells 5 of the cartridge 1 may comprise such a top piercing system 60 depending on the requirements of the task the cartridge 1 is designed for.

The at least one top piercing system 60 comprises at least a piston 61 and a piercing element 13. Preferably, the piercing element is configured as a thorn 63 located at a lower front side 74 of the piston 61.

The piston 61 is configured to be movable within the well 5 while providing a seal between the piston 61 and the inner wall of the well 5. Thus, the piston 61 may sealingly close the top opening 72 of the well 5 for example when being positioned in a storage position. More particularly, the piston 61 with the thorn 63 is movable up and down between the top opening 72 and the bottom opening 73 of the well 5 the piston 61 is integrated. Preferably, the piston 61 is adopted in its width to sealingly move along the side walls of the well 5. For this, the piston 61 may comprise a gasket 62 that provides the sealing connection to the side wall of the well 5, as it is shown in FIG. 10. Alternatively, the piston 61 may be manufactured in a size and from a material that directly provides for the sealing connection (not shown). Such a material may be a deformable polymer like rubber or silicone. In a further alternative embodiment, a flexibly deformable top structure 7 is sealingly attached to the upper surface 3 of the body and an upper actuation side 77 of the piston 61, as shown on the left side of FIG. 14. The height of the piston 61 and thorn 63 is adopted so that in a storage position, the piston 61 with its actuation side 77, which is preferably abutted to move the piston 61 within the well 5, is essentially flush with the upper surface 3 of the body 2 while the tip of the thorn 63 is in a safe distance to the piercable bottom structure 8 or the piercable foil 79 respectively. Furthermore, the height of the piston 61 and thorn 63 are adopted, so that in a piercing position, the tip of the thorn 63 has opened the piercable bottom foil and projects into the gap 12 or into an additionally provided relief space, while the piston 61 remains sealing the top opening 72 of the well 5 independently of the shape of the well 5.

Figure 11A:
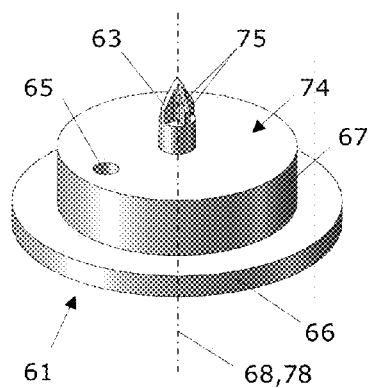
FIG. 11A a 3D view of a top piercing system with the piston having a Phillips head shaped thorn and a through hole.

In FIG. 11, a selection of various exemplary embodiments of the top piercing system 60 according to the present invention comprising a combination of a piston 61 and a thorn 63 are shown:

In FIG. 11A, a 3D view of the top piercing system 60 comprising the piston 61 with the thorn 63 is shown. This 3D view shows the piston 61 with the thorn 63 upside down compared to its position within a well 5 of a cartridge 1 as shown in the FIGS. 10, 13 and 14, to allow a better illustration of the thorn 63. The thorn 63 here is accomplished to be Phillips head shaped with guiding channels 75. This embodiment of the thorn 63 is particularly preferred as it allows the liquid to pass the thorn 63 through its guiding channels 75 when the thorn 63 is already in a piercing position, thus when the thorn 63 has pierced the piercable bottom structure 8 or the piercable foil 79 respectively of the cartridge 1. The piston 61 shown in FIG. 11A is manufactured as a single injection molded piece, comprising a larger upper part 66 with an actuation side 77 with which the piston 61 may be aligned essentially flush with the upper surface of the body 2, and a smaller lower part 67 with the front side 74 to which the thorn 63 is attached and which may abut the bottom of the well 5 the piston 61 with the thorn 63 is inserted. The upper and the lower part 66,67 shown here are cylindrically shaped and are adopted in their size relative to each other so that they form a flange in which a gasket 62 may be placed. For illustrational purposes, the gasket 62 is not shown here (please compare with FIG. 11F).

The top piercing system 60 shown in FIG. 11A further comprises a through hole 65 which extends through the entire piston 61. This through hole 65 provides a pressure relief channel which is necessary when the manufacturing process of producing the cartridge 1 requires that firstly, the body and the piercable bottom structure 8 are attached to each other, then a liquid is filled into one or more selected wells 5, and only in a last step, a piston 61 with the thorn 63 is inserted into a filled well 5. In this process, the through hole 65 is required, as the excess air needs to be vented from the well 5 when the piston 61 is inserted. Afterwards, the through hole 65 must be sealed. Alternatively, and more preferred, the manufacturing process of the cartridge 1 includes in a first step the insertion of the piston 61 with the thorn 63 and eventually with a gasket 62 into the selected well 5, thereby sealingly closing the top opening 72 of the well 5. Afterwards, the body 2,2',2" may be turned upside down for filling the liquid 6 into that well 5. Here, in a last step, the bottom opening 73 of the well 5 is sealed by attaching the piercable foil 79. In this more preferred manufacturing process, a through hole 65 must be avoided in the piston 61, as it would allow the introduced liquid to leak out when sealing the bottom opening 73 of the well 5.

The FIGS. 11B to 11G show selected alternative embodiments of the top piercing system 60 according to the present invention in vertical cross sections. In all embodiments shown here, the top piercing system 60 comprises the piston 61, the thorn 63 and at least one gasket 62. An actuation side 77 of the piston 61, which is preferably abutted for moving the piston 61 within the well 5, is also indicated.

The 3-dimensional form of the piston 61 is adopted in size and shape to the inner dimensions of the well 5, into which the piston 61 shall be integrated as a part of a top piercing system 60. Thus, when a well 5, into which a top piercing system 60 shall be inserted, is cylindrically formed in its inner dimensions with a circular base and a flat inner bottom 76; preferably, the piston 61 is complementarily formed essentially cylindrically with a circular base. Furthermore, the front side 74 of the piston 61, which preferably abuts the inner bottom 76 of the well 5 in the piercing position, is also configured as a complementary flat front side 74. Such a flat front side 74 of the piston 61 is shown in the FIGS. 11A, 11B and 11C. In case the inner bottom 76 of the well 5 is tapered; preferably, the front side 74 of the piston 61 is correspondingly tapered too. Accordingly, the whole front side 74 of the piston 61 may abut the tapered inner bottom 76 of the well 5. Such a correspondingly tapered front side 74 of the piston 61 is shown in the FIGS. 11D-G. If required, the front side 74 of the piston 61 may comprise more than one tapered surfaces which form an offset in the area where they adjoin each other (not shown). Thus, the front side 74 of the piston 61 of the at least one top piercing system 60 is adapted in shape to the shape of an inner bottom 76 of the well 5 into which the top piercing system 60 is integrated. In any case, the outer dimension of the piston 61 is preferably adapted to the inner dimension of the well 5 so that the piston 61 is movable within that well 5 while sealingly closing the top opening 72 of the well 5.

The 3-dimensional form of the thorn 63 is adopted to pierce the piercable bottom structure 8 for releasing a reagent or sample 6,6' from the well 5 into the gap upon moving the piston 61 within the well 5 towards its bottom opening 73.

Preferably, the ability of the piston 61 to sealingly close the top opening 72 of the well is provided by a gasket 62 which is tightly attached to the piston 61. In the FIGS. 11B-11G, each piston 61 shown has at least one gasket 62. Preferably, the gasket 62 is shaped as an O-ring which completely surrounds an outer side of the piston 61. The gasket 62 is preferably attached to the upper part 66 of the piston 61 for sealingly abutting the inner wall of the well 5. By the upper part 66 of the piston 61 which projects over the lower part of the piston 61, a flange is formed to which the gasket 62 may be attached (see FIGS. 11F and 11G). Alternatively, the gasket 62 may be positioned in a circular groove of the piston 61 which is formed at least by its upper part 66 (see FIGS. 11B-11E). The flange and the circular groove are means to secure that the gasket 62 remains on the piston 61 when the piston 61 is moved within the well 5. Other means for securing a gasket 62 on a piston 61 known in the art may be used were appropriate.

Figure 11B:
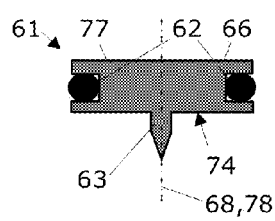
FIG. 11B a piston-thorn combination made in one piece, the piston having a circular groove for receiving a gasket and being configured relatively flat.
Figure 11C:
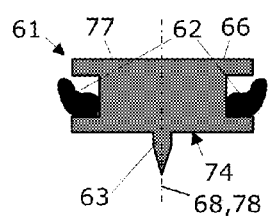
FIG. 11C a piston-thorn combination made in one piece, the piston having a circular groove for receiving a gasket in form of a lip seal.
Figure 11D:
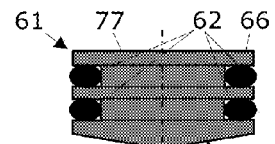
FIG. 11D a piston with a thorn at its lower front, the piston being composed of multiple parts and having circular grooves for receiving in each groove a gasket.
Figure 11E:
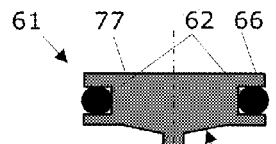
FIG. 11E a piston-thorn combination made in one piece, the piston having a circular groove for receiving a gasket, while the front side of the piston comprises a tapered portion.

The choice of the form of the gasket 62 for providing the seal while still enabling a movement of the piston 61 is known in the art. To mention some forms which are suitable for a top piercing system 60 according to the present invention without restricting the gasket 62 to these forms, such selected forms shall here exemplarily be mentioned: the FIGS. 11B, 11D, 11E show a gasket 62 which is accomplished as a typical O-ring known in the art. The FIG. 11C shows a gasket 62 which is configured as a lip seal. The FIG. 11F shows a gasket 62 accomplished as an O-ring (left) or a quad-ring (right), while FIG. 11G shows a gasket 62 accomplished as a bellow seal. Particularly a gasket 62 accomplished as a bellow seal might be preferred as it is known to provide for a good sealing quality without providing significant friction resistance. This would facilitate the movement of the piston 61 within the well 5.

The piston 61 may also comprise more than one gasket 62, as shown in FIG. 11D. A piston 61 having e.g. two separate gaskets 62 would provide an increased sealing surface which abuts the inner side of the wall of the well 5. However, this embodiment has the disadvantage that the friction resistance which is generated upon the movement of the piston 61 within the well 5 is increased. In any case, the form and number of gaskets 62 attached to a piston 61 of the top piercing system 60 has to be chosen to balance the requirement of a tight closure of the top opening 72 of the well 5 while still enabling the movement of the piston 61 within the well using reasonable driving forces, thus, enabling e.g. manual or motorized pressing down the piston 61 e.g. by using a finger or an actuating element 41 (see FIG. 14). This balance not only ensures that no liquid may leak out of the well 5, but additionally that an overpressure is generated within the well 5 upon the movement of the piston 61 towards the bottom opening 73 of the well 5. This overpressure provides an important force which enables the release of the liquid (be it a reagent or a sample 6,6') from the well into the gap 12 when the thorn 63 of the top piercing system 60 has pierced the piercable bottom structure 8. Suitable materials for a gasket 42 are known in the art; typically, rubber is preferred. Exemplarily, Neoprene® and Viton® are mentioned here as O-ring material.

As may further be taken from the FIGS. 11B-11G, and as it is particularly preferred, the piston 61 and the thorn 63 may be produced in one piece, e.g. by injection molding. This is shown in the FIGS. 11B, 11C, 11E, and 11G. As a suitable material for producing the piston 61 and thorn 63 as a single piece is Polypropylene. Alternatively, the piston 61 and the thorn 63 may be produced in multiple separate pieces in a first step and afterward, the single pieces are attached to each other e.g. by gluing, welding, or press fit, as it is shown in FIGS. 11D and 11F. According to FIG. 11F, the thorn 63 may be produced from a different material that the piston 61. For example, the thorn 63 may be produced from a metal or another strong material for facilitating the piercing of the piercable bottom structure 8. Such a thorn 63 made of metal may be inserted into the molding form before the piston parts are produced by backmolding.

The thorn 63 is located at the front side 74 of the piston 61 and is configured to pierce the piercable bottom structure 8, i.e. the piercable foil 79 for releasing a reagent or sample 6,6' from said well 5 into the gap 12 upon moving the piston 61 within the well 5 toward the bottom opening of that well 5. For this, the thorn 63 comprises at its lower end a tip portion 70 with a tip that is firstly abutted to the piercable foil 79 when the piston 61 has been moved far enough within the well 5 and, when the piston 61 is moved further towards the bottom opening 73 of the well 5, pierces the piercable foil 79.

To provide a good transfer of the force, with which the piston 61 is moved toward the bottom opening 73 of the well 5 (which may be manually or automatically), to the tip of the thorn 63 for piercing, the thorn 63 is in a preferred embodiment located centrically on the front side 74 of the piston 61. In this case, the longitudinal axis 68 of the thorn 63 runs congruent with the longitudinal axis 78 of the piston 61. This is shown in the FIGS. 11A-11F and H, and in the FIGS. 10, 13, and 14. Alternatively, the thorn 63 is located eccentrically on the front side 74 of the piston 61. Here, the thorn 63 may be located on the piston 61 so that the longitudinal axes 68,78 of the piston 61 and thorn 63 run parallel to each other (not shown), or the thorn 63 is located on the piston 61 so that its longitudinal axis 68 is tilted to the longitudinal axis 78 of the piston 61 by an angle. This situation is shown in FIG. 11G. Here, though the thorn 63 is arranged with its longitudinal axis 68 in an angle with respect to the longitudinal axis 78 of the piston 61, the tip of the thorn 63 remains to be located on the longitudinal axis 78 of the piston 61. However, the thorn 63 may be arranged eccentrically so that the tip of the thorn 63 is also off-center with respect to the piston 61. A tilted positioning of the thorn 63 with respect to the longitudinal axis 78 of the piston 61 has the advantage that upon piercing, a broader opening within the piercable foil 79 is generated through which the liquid may simply flow out without the need of additional guiding elements.

Figure 11H:
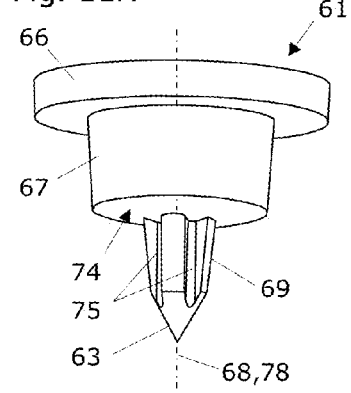
FIG. 11H a 3D view of a top piercing system with a Philips head shaped thorn, the lower part of the piston and the thorn having a frustoconical shape.
Figure 11F:
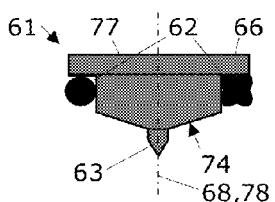
FIG. 11F a piston with a thorn at its lower front, made of multiple parts, the piston having an flange for receiving a quad-ring or an o-ring as a gasket, and a front side with a tapered portion.
Figure 11G:
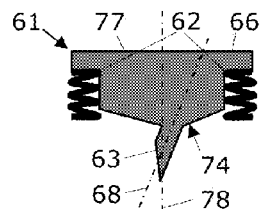
FIG. 11G a piston-thorn combination made in one piece, the piston having a flange for receiving a gasket in the form of a bellow, with the thorn being connected to the piston in that its longitudinal axis runs in an angle with respect to the longitudinal axis of the piston.

In FIG. 11H, a 3D view of a top piercing system 60 in a particularly preferred embodiment is shown. In contrast to FIG. 11A, the lower part 67 of the piston 61 has a frustoconical shape. Furthermore, the thorn 63 has a neck portion 69 which is frustoconically shaped, too. This is particularly preferred as the frustoconical shape enables an easier demolding of the piston 61 with thorn 63 in the production process. The front side 74 of the piston 61 is tapered. Correspondingly, the well 5, into which the piston 61 with the thorn 63 shall be inserted, is shaped complementarily, having complementarily frustoconically shaped inner walls and a complementarily tapered inner bottom 76 (not shown here). The thorn 63 is Philips-head shaped, with the guiding channels 75 extending over the entire height of the thorn 63. The upper part 66 of the piston 61 shown in FIG. 10 however has a cylindrical shape, and forms together with the lower part 67 a flange in which a gasket 62 may be placed. The longitudinal axis 68 of the thorn 63 runs congruent with the longitudinal axis 78 of the piston 61.

The top piercing system 60 which comprises a piston 61 with a thorn 63, is accomplished to be positionable within a well 5 of the body 2. The top piercing system 60 is preferably accomplished for wells 5 which are sized to take up a liquid sample volume of 10-400 µl, most preferably of 20-50 µl. Exemplarily, such wells are configured being 5-20 mm in diameter and 5-20 mm deep, most preferably 7 mm in diameter and 8 mm deep. Correspondingly, a piston 61 with a thorn 63 would be adapted in size to fit into such a well 5, which would in this case be most preferably 7 mm in diameter and 8 mm deep.

Suitable reagents 6 or samples 6' which may be hold or stored in a well 5 and released therefrom using a top piercing system 60 according to the present invention are for example wash liquids, buffers, master mixes, or other used e.g. in PCR amplification or hybridization experiments as described above. Furthermore, oils which are for example used for partially or entirely filling the gap 12 prior to enter sample droplets 23 into the gap 12, and which are inert (e.g. silicon oil) and not miscible with the samples, may be hold or stored in one or more wells 5 comprising the top piercing system 60. Particularly useful storable liquids are such liquids which are stable upon storage at room temperature. In case a reagent 6 or sample 6' has to be stored in a well 5 comprising a top piercing system 60 at a lower temperature such as 4° C. or −20° C., preferably the whole cartridge 1 is stored at that temperature, too. Otherwise, if a reagent 6 or sample 6' which is stored in such a well 5 has to be heated, e.g. prior to its release into the gap 12, the whole cartridge 1 may be heated correspondingly. In this case, the materials of the cartridge components may be chosen so that the cartridge might be exposed to temperatures e.g. up to 70° C.

In FIG. 12, an overview of different selected embodiments of the thorn 63 is given. The thorn 63 is located at a front side 74 of the piston 61 (the piston 61 is not shown here) and is configured to pierce the piercable bottom structure 8 for releasing a liquid (a reagent or sample 6,6') from the well 5 when the piston 61 with the thorn 63 are moved within the well 5 towards its bottom opening 73.

In its simplest embodiment, the thorn 63 is cone-shaped (not shown), and is attached to the front side 74 of the piston 61 with its base, so that the tip is directed towards the bottom opening 73 of the well 5 into which the top piercing system 60 is inserted. Upon movement of the piston 61, the thorn 63 is guided through the bottom opening 73 of the well 5 and onto the piercable foil 79. Upon further movement of the piston 61 toward the bottom opening 73 of the well 5, the tip of the thorn 63 disrupts the piercable foil 79 which has sealed the bottom opening 73 of the well, and is guided at least partially through the piercable foil 79, too. Thereby, the piercable foil 79 is opened, and a fluid path is provided so that the reagent or sample 6,6' may be released from the well 5 into the gap 12. In this case, the piercable foil 79 preferably is made of a non-elastic material.

Figure 12A:
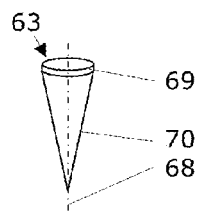
FIG. 12A a thorn having a short cylindrical neck portion and a long cone-shaped tip portion.
Figure 12B:
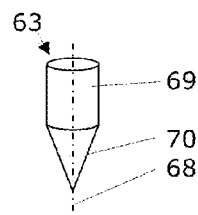
FIG. 12B a thorn having a longer cylindrical neck portion and a shorter, cone-shaped tip portion.
Figure 12C:
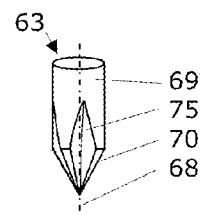
FIG. 12C a thorn having a cylindrical neck portion and a Phillips head-shaped tip portion.
Figure 12D:
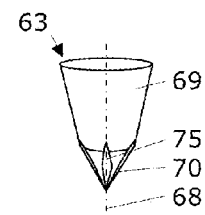
FIG. 12D a thorn having a conical neck portion and a short Phillips head shaped tip portion.
Figure 12E:
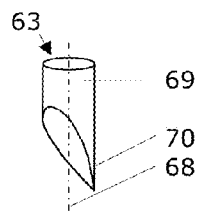
FIG. 12E a thorn having a cylindrical neck portion and an off-center tip, which is cut from the neck by an oblique plane.
Figure 12F:
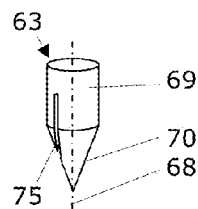
FIG. 12F a thorn having a short cylindrical neck portion and a long cone-shaped tip portion as shown in FIG. 12A, having additionally a guiding channel located eccentrically to the tip.
Figure 12G:
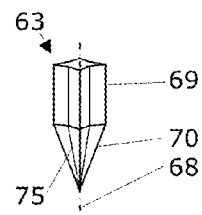
FIG. 12G a thorn having a neck portion and a tip portion on a star-like bases with guiding channels provided by the inner edges of the star.

In a more preferred embodiment, the thorn 63 comprises a neck portion 69 and a tip portion 70 with the tip, as shown in the FIGS. 12A-12F, and 12H. The thorn 63 is connected with or attached to the front side 74 of the piston 61 with the base of its neck portion 69, while the tip is directed towards the bottom opening 73 of the well 5 when the piston 61 with the thorn 63 is inserted. Preferably, the neck portion 69 is cylindrically or frustoconically shaped. A thorn 63 having a frustoconical neck portion 69 is shown in FIG. 11H. The use of such a neck portion 69 provides more stability to the unit of piston 61 and thorn 63 particularly when the tip of the thorn pierces the piercable foil 79. The basis of the cylinder may be a circle, as shown in the FIGS. 12A-12F, and 12H. The basis of the neck portion 69 may however be another than a circle, for example may be a triangle, a rectangle or may be configured star-like, with two, three or more tips. In FIG. 12G, exemplarily a thorn 63 having a star-like base with four tips and a cone-shaped tip portion with the same star-like base is shown.

The height of the neck portion 69 and the height of the tip portion 70 may vary depending e.g. on the height of the well 5, on the friction resistance which is generated upon moving the piston 61 within the well 5, and on the strength/material of the piercable foil 79.

In a particular preferred embodiment of the thorn 63, the tip portion 70 of the thorn 63 is configured to be cone-shaped, as it is shown in the FIGS. 12A-12D, 12F, and 12G. Alternatively, the tip of the thorn 63 may be generated upon tapering/beveling the tip portion 70, so that the tip is positioned off-center with respect to the longitudinal axis 68 of the thorn 63, as it is shown in the FIGS. 12E and 12H.

Preferably, the thorn 63 comprises at least one guiding channel 75. More preferably, the at least one guiding channel 75 is located at the tip portion 70 of the thorn 63, but may project into the neck portion 69 of the thorn 63. The presence of one or more guiding channels 75 is preferred as it simplifies the release of the reagent or sample 6,6' from the well 5 into the gap 12: Each guiding channel 75 provides an outlet or fluid path which allows the release of the oil, liquid reagent or sample from the well 5 through that outlet when the tip of the thorn 63 has pierced the piercable foil 79 and penetrates it. Due to the overpressure which is generated by the movement of the piston 61 within the well 5 towards the bottom opening 73, the liquid may be pressed out of the well, guided by the guiding channels 75.

Figure 12H:
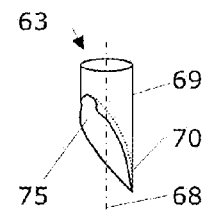
FIG. 12H a thorn having a cylindrical neck portion and an off-center tip, which is similarly formed as shown in FIG. 12E, but with an additional chamfer.

In a preferred embodiment, guiding channels 75 are provided in that the tip portion 70 or the complete thorn 63 is provided in a Phillips-head shape. This is shown in the FIGS. 12C and 12D and in FIG. 11H. Alternatively, a guiding channel 75 may be accomplished as an eccentric slit which might extend over the entire cross-sectional dimension at least of the tip portion 70 of the thorn 63. Such an eccentric guiding slit is shown exemplarily in the FIG. 12F. Otherwise, guiding channel 75 may be provided by the basic form chosen for the thorn 63, as may be seen in the FIG. 12G. Here, the inner edges of the star-like neck and tip portion provide the guiding channels 75 which allow the flow of the liquid reagent or sample 6,6' when the thorn 63 has pierced the piercable foil 79. In FIG. 12H, the thorn 63 comprises a chamfer which acts as a guiding channel 75.

Nevertheless, also in the case the thorn 63 does not comprise a guiding channel 75, the reagent or sample 6,6' may be released of the well 5. Release is here enabled by an erratic opening which is generated in the piercable foil 79 upon piercing, in particular when the piercable foil 79 is of a non-elastic material. The release may further be enabled by a backward movement of the piston 61 after the thorn 63 has pierced the piercable foil 79. This backward movement is caused by the gasket 62 of the piston 61, which is deformed during the movement of the piston 61 towards the bottom opening 73. When the piston 61 and the thorn 63 are arrived in the piercing position, the gasket 62 tends to deform back towards its original shape, thereby the piston 61 with the thorn 63 are slightly moved back into the well 5. This then provides a space between the thorn 63 and the piercable foil 79, through which the liquid reagent or sample 6,6' may flow out.

In FIG. 13, a vertical cross section through a cartridge 1 in the fifth embodiment according to the present invention comprising alternative top piercing systems 60 is shown. The cartridge 1 is not yet in contact with the electrode array 20 of a system 40 for liquid droplet manipulation, but is presented in a confirmation that is suitable for being stored or transported: In the embodiment shown, the cartridge 1 comprises a plate-like body 2,2' and a working film 10 for manipulating samples with the electrode array 20, wherein the working film 10 is configured as a monolayer which is impermeable to liquids, which comprises a hydrophobic upper surface 11, and which provides for the electrical insulation of the electrodes 44 of the electrode array when the cartridge 1 is placed with its working film 10 on that array 20.

Alternatively, the body 2 of the cartridge 1 may be configured as a frame structure 2" with a central opening 14, which is closed by a bottom portion 16, or with a central opening 14 that extends across the entire height of the body 2,2", as discussed above. The body 2,2' comprises at least one well 5, each well 5 comprising a top opening 72 at the upper surface 3 of the body 2,2',2", a bottom opening 73 at the lower surface 4 of the body 2,2',2", and an inner bottom 76.

The working film 10 exemplarily shown in FIG. 10 is of a material that is heat shrinkable and sized so that it may be used as an overall closure for the cartridge 1. For this, the working film 10 is wrapped around the whole cartridge and is afterwards shrunk by the application of heat to provide for the tight closure. The working film 10 can be heat shrunk by exposing it to a heat gun which blows air hot enough to shrink the film. In this way, it is ensured that no liquids, which are provided by the cartridge 1, may leak out during transportation or storage, for example. A suitable material for such a heat-shrinkable working film 10 is for example a linear COP with a low crystallinity, or a heat-shrinkable PE. It is clear to a skilled person that the working film 10 may be accomplished in other embodiments which were discussed before, depending on the requirements for the cartridge 1 and the electrode array 20.

The cartridge 1 shown in FIG. 13 also comprises at least one peripheral spacer 9 and an intermediate spacer 15 in embodiments and combinations thereof as discussed previously. The cartridge 1 also comprises a piercable bottom structure 8 that is configured as a piercable foil 79 which is sealingly attached to the lower surface 4 of the body 2,2'. Furthermore, the cartridge 1 shown comprises at least two wells 5, each with a top piercing system 60. The two wells 5 are filled partially with a reagent or sample 6,6'. It is indicated by two dotted, parallel, essentially vertical wave-like lines that not a complete cartridge is shown, but only two sections which are of particular interest for the description of a top piercing system 60 according to the present invention.

The piercable foil 79 shown in FIG. 13 is not configured as a piercable cover layer 79' which closes the gap 12 on a side opposite to the working film 10, as shown in FIG. 10. Instead, the cartridge 1 comprises an additional rigid cover 17, which closes the gap 12 and which provides the hydrophobic upper surface of the gap 12. The hydrophobic surface may be provided directly be the material of the rigid cover 17, or may be provided by an additional coating of the lower surface of the rigid cover 17 which closes the gap 12.

Exemplarily, such a coating may be a Teflon® coating which is applied to the lower surface of the rigid cover 17 e.g. by spincoating.

Optionally, this rigid cover 17 may be coated on its underside or upper side with an electrically conductive layer that may be (or may be not) connected to a ground potential source of the system 40 for liquid droplet manipulation. A suitable coating may be provided using indium tin oxide (ITO). However, such an electrically conductive coating is not necessary for manipulating droplets by electrowetting techniques. In the embodiment shown in FIG. 13, the hydrophobic upper surface of the gap 12 is provided by the rigid cover 17.

The cartridge 1 presented in FIG. 13 further comprises an additional thorn relief spacer layer 64 which is positioned between the piercable foil 79 and the rigid cover 17. The thorn relief spacer layer 64 comprises a relief opening 71 which is positioned below the bottom opening 73 of the well 5 comprising a top piercing system 60 according to the present invention. In this way, the thorn relief spacer layer 64 with its relief opening 71 provides an additional space which may accommodate the tip of the thorn 63 when penetrating the piercable foil 79 after piercing the piercable bottom structure 8; thus, preventing that the thorn 63 reaches the working layer 10 and eventually damages its upper surface 11. Additionally, the relief opening 71 provides an outlet path and thereby guidance for the oil, liquid reagent or sample 6'6" which has been released from the well 5 upon piercing the piercable foil 79.

The thorn relief spacer layer 64 is attached to the lower side of the piercable bottom structure 8, i.e. the piercable foil 79, and to the rigid cover 17 by e.g. gluing or (laser) welding. For gluing, an adhesive tape may be used, for example.

The thorn relief spacer layer 64 is preferably made of a material which may be sealed to the piercable foil 79 and the rigid cover 17, which is not swelling upon the contact with a liquid and which has good dimensional stability properties. Exemplarily, gasket material such as polyethylene-terephthalat modified with glycol (PETG) shall be mentioned here; alternatively, acrylic or other (cheaper) material with similar properties may be used.

The thickness of the thorn relief spacer layer 64 may be adapted to the design of the well 5, particularly to the design of the bottom opening 73, to the length of the thorn 63, and to the distance the piston 61 shall move between the storage position and the piercing position. Preferably, the thorn relief spacer layer 64 has a thickness of 0.2-0.7 mm, more preferably of 0.4-0.6 mm.

The thickness of the rigid cover 17 preferably is adapted to the thickness of the thorn relief spacer layer 64 and of the piercable foil 79. In a preferred embodiment, these three layers result in a total height of about 0.4-1.9 mm, when sealingly attached to each other. In a particularly preferred embodiment of a cartridge 1 comprising the piercable foil 79, the thorn relief spacer layer 64 and a rigid cover 17, as shown in FIG. 13, the rigid cover 17 is configured as a thinner film of about 200 µm, and is made of Mylar®, which is a transparent, flexible polyester foil on the basis of polyethylene terephthalat from DuPont. Alternatively, the rigid cover 17 may be made of acrylic. This allows the provision of a thicker rigid cover 17, which would increase the stability to the cartridge 1. Such a thicker rigid cover 17 might be desired when the body 2 of the cartridge 1 is configured as a frame structure 2" with a central opening that extends across the entire height of the body 2,2". Such a thicker rigid cover 17 might even replace the thorn relief spacer layer 64 when it is provided with an appropriate thickness (which is e.g. up to 1.6 mm). This embodiment is discussed in FIG. 14.

The rigid cover 17 is attached to a lower side of the thorn relief spacer layer 64. Thereby, the rigid cover 17 encloses the gap 12 on a side opposite to the working film 10. For the release of the reagent or sample 6,6' from the well 5, not only the thorn relief spacer layer 64 but additionally the rigid cover layer 17 has to comprise an opening below a well 5 which comprises a top piercing system 60 according to the present invention, which allows the liquid to flow from the well 5 into the gap 12. This opening is provided by the cover hole 18. Thus, the rigid cover 17 comprises at least one cover hole 18 which is situated below the bottom opening 73 of the well 5 and below the relief opening 71 of the thorn relief spacer layer 64.

Both, the relief opening 71 and the cover hole 18 may be configured to have essentially the same diameter and being arranged one upon the other, so that they form a single path for the released liquid reagent or sample 6,6' below the bottom opening 73 of the well 5. This situation is exemplarily shown for the well 5 at the right side of the cartridge 1 of FIG. 13. Alternatively, the relief opening 71 and the cover hole 18 may be shifted by a distance to each other, so that they still provide a continuous opening through which the liquid reagent or sample 6,6' may flow from the well 5 into the gap 12. The provision of such a lateral adjustment is a simple method to guide the released liquid into a desired direction through the layers 64,17 into the gap 12. This situation is shown for the well 5 at the left side of the cartridge 1 of FIG. 13. Though the relief opening 71 and the cover hole 18 may be configured having essentially the same diameter, also when they are shifted to each other, they may alternatively vary in their diameter, as it is shown for the left well 5. Here, the cover hole 18 is configured as an elongated slit for guiding liquid to a position on the working film which is aside from the bottom opening 73 of well 5 and from the relief opening 71 of thorn relief spacer layer 64.

In FIG. 13, two alternative embodiments of a top piercing system 60, each inserted into a well 5 of the body 2 of the cartridge 1 are shown:

On the right side, a cartridge 1 is shown with the piston 61 and the body 2,2', both being produced as separate pieces, with the piston 61 comprising the gasket 62, as discussed above. On the left side, the body 2,2' and the piston 61 are produced in a two-component injection molding process, so that the body 2,2' and the piston 61 are produced from a first material, while the gasket 62 is produced e.g. from a second, elastomeric material that connects the body 2,2' with the piston 61. Such an embodiment of the body 2,2' and the piston 61 typically requires the production in two parts: an upper part which comprises the upper part of the body, the gasket 62 and the piston 61, and a lower part comprising the lower part of the body 2. Both parts may then be joined along a mold separation line (indicated by the dotted horizontal line on the left side of the cartridge 1) e.g. by friction welding or gluing. It is clear to a skilled person that this embodiment shown on the left side of the cartridge 1 in FIG. 13 is suitable for a body 2 which is configured in a plate-like structure 2' or a frame structure 2" equally.

As discussed above, the form of the piston 61 is adopted to the inner dimensions of the well 5, into which the top piercing system 60 shall be integrated. In FIG. 13, the two wells 5 are shown having a tapered bottom. Consequently, the front side 74 of the piston 61 is also tapered complementarily, so that the piston 61 may abut the bottom of the well 5 with its front side 74 to stop the movement of the piston 61 within the well 5 toward its bottom opening 73 in a piercing position. Alternatively, the bottom of the well 5 may comprise one or more guiding bars which may be abutted by the front side 74 of the piston 61, and which help guiding the liquid reagent or sample 6,6' towards the bottom opening 73 of the well 5 when the internal pressure in the well 5 rises upon the movement of the top piercing system 60 within the well 5 towards its bottom opening 73 (not shown). The actuation side 77 of the piston 61, which is preferably abutted for moving the piston 61 within the well 5, is also indicated.

FIG. 14 shows a vertical cross section through selected parts of a plate-like structured cartridge 1 in the fifth embodiment according to the present invention, comprising alternative embodiments of the top piercing system 60, and alternative embodiments of the foils between the body 2 and the spacer 9:

The cartridge 1 is shown to be in contact with the electrode array 20 of a system 40 for liquid droplet manipulation. The body 2 of the cartridge 1 is configured as a plate-like structure 2'. Alternatively, and as discussed before, the body 2 of the cartridge 1 may be configured as a frame structure 2" with a central opening 14, which is closed by a bottom portion 16, or with a central opening 14 that extends across the entire height of the body 2,2", as discussed above. The body 2,2' comprises at least one well 5. Each well 5 comprises a top opening 72 at the upper surface 3 of the body 2,2',2", a bottom opening 73 at the lower surface 4 of the body 2,2',2", and an inner bottom 76.

Two selected parts of the cartridge 1 are shown in this FIG. 14, each part comprising a well 5 having a top piercing system 60 of different embodiments according to present invention. It is again indicated by two parallel dotted, vertical wavelike lines that not a complete cartridge is shown but only the selected sections which are of particular interest of the description of a top piercing system 60 of the present invention.

The cartridge 1 shown in FIG. 14 comprises a working film 10 which is configured as a monolayer of a hydrophobic material which is not electrically insulating. To avoid a shortage between the individual electrodes 44 of the electrode array 20, an additional dielectric layer is required that is located between the electrode array 20 and the working film 10 when the cartridge 1 with the working film 10 is placed on the electrode array 20. This additional dielectric layer may be positioned on the electrode array 20 before the cartridge 1 is placed thereon with its working film 10, or alternatively, the dielectric film 50 is attached to the working film 10, as discussed previously. It may also be preferred providing the electrode array 20 with a permanent cover from dielectric material that protects the electrodes from oxidation and contamination. In FIG. 14, a dielectric layer is shown which is configured as a separate electrically insulating film 50, which coats the electrodes 44 and substrate 42 of the system 40 for liquid droplet manipulation. The coating may be irremovable or removable, depending on the need, as discussed above. The preferred material for a working film of a monolayer of hydrophobic non-dielectric material is for example polytetrafluorethylene or polytetrafluorethen (PTFE), as discussed above.

The cartridge 1 shown in FIG. 14 further comprises at least one peripheral spacer 9 that is located below the lower surface 4 of the body 2,2' and that connects the working film 10 to the body 2,2'. The cartridge 1 also comprises a gap 12 between the lower surface of the body 2,2' and the hydrophobic upper surface 11 of the working film 10. This gap 12 is defined by the peripheral spacer 9. The peripheral spacer 9 here is attached to the rigid cover 17. The cartridge 1 shown in FIG. 14 further comprises at least one intermediate spacer 15 that is located within the area of the gap 12. This at least one intermediate spacer preferably has the same height as the peripheral spacer 9 and preferably defines the same gap height, as discussed before.

The cartridge 1 also comprises the piercable bottom structure 8 which is accomplished as a piercable foil 79. This piercable foil 79 is sealingly attached to the lower surface 4 of the body 2,2", is impermeable to liquids and is configured to seal the bottom opening 73 of at least one well 5, which preferably comprises a top piercing system 60 according to the present invention. E.g. depending on a required partitioning of the gap 12 by the spacers 9,15, the piercable foil 79 may be sized to seal one or more well 5 of the cartridge, independently, whether these wells 5 comprise a top piercing system 60 or not. The piercable foil 79 may alternatively be sized to completely cover the lower surface 4 of the body 2 of the cartridge 1, sealing all wells 5, as discussed before.

The cartridge 1 shown in FIG. 14 further comprises a rigid cover 17, which is attached to the lower side of the piercable foil 79, e.g. by gluing of welding. The rigid cover 17 may be coated on its underside with an electrically conductive layer that may be connected to a ground potential source of the system 40 for liquid droplet manipulation. A suitable coating may be provided using indium tin oxide (ITO). However, the electrically conductive coating is not necessary for carrying out droplet manipulations by electrowetting techniques.

As in the embodiment shown in FIG. 13, the hydrophobic upper surface of the gap 12 in the embodiment shown in FIG. 14 is provided by the rigid cover 17. The hydrophobic surface may be provided directly be the material of the rigid cover 17, or may be provided by an additional coating of the lower surface of the rigid cover 17 which closes the gap 12. Exemplarily, such a coating may be a Teflon® coating which is applied to the lower surface of the rigid cover 17 e.g. by spincoating. The rigid cover 17 comprises a cover hole 18 which is located below the bottom opening 73 of the well 5 which comprises a top piercing system 60, as previously discussed.

The cartridge 1 shown in FIG. 14 does not comprise an additional thorn relief spacer layer 64. Instead, the cover hole 18 of the rigid cover 17 is used as an additional space for accommodating the tip of the thorn 63. Thus, in the embodiments shown in FIG. 14, the cover hole 18 of the rigid cover 17 is used to prevent that the thorn 63 reaches the working layer 10 and eventually damages its upper surface 11 when the top piercing system 60 has been moved into the piercing position (thus, when the thorn 63 has pierced the piercable foil 79 and the piston 61 abuts or is about to abut the bottom of the well 5). Additionally, the length of the thorn 63 and the size of the piston 61 may be adapted to the height of the gap 12 and the height of the rigid cover 17 (or vice versa).

As discussed before, the height of the rigid cover 17 may further be adapted to the embodiment of the body 2: a thicker rigid cover 17 might be desired when the body 2 of the cartridge 1 is configured as a frame structure 2" with a central opening that extends across the entire height of the body 2,2". Here, a thicker rigid cover 17 would improve the dimensional stability of the cartridge 1 while providing a relief space for the thorn 63. On the other hand, a thinner rigid cover 17 might be desired e.g. when the body 2 is configured as a plate-like structure 2', which inherently is more stable than a frame structured body.

Preferably, the height of the rigid cover 17 is 0.2-1.8 mm, more preferably of 0.4-1.5 mm. In a particularly preferred embodiment, the rigid cover 17 has a height (or a thickness, respectively) of 1.5 mm.

In the embodiment of the top piercing system 60 shown on the left side of the cartridge 1, the piston 61 with the thorn 63 has just left the storage position. The piston 61 does not comprise a gasket 62. Instead, the piston 61 is manufactured in a size and from a material that directly provides for the sealing connection to the side wall of the well 5, and the cartridge 1 comprises a flexibly deformable top structure 7, which sealingly covers the top opening 72 of the well 5 which comprises the top piercing system 60. For keeping the piston 61 in a controllable position within the well 5, the piston 61 is preferably glued to the flexibly deformable stop structure 7 with its actuation side 77. In this way, the piston 61 is movable within the well 5 by applying a pressure on the upper surface of the flexibly deformable top structure 7. For reducing the friction between the piston 61 and the inner side of the wall of the well 5 upon the movement of the piston 61, the piston 61 may be coated with an anti-friction coating at least on its sides which contact the inner wall of the well 5 (not shown). Such an anti-friction coating might be for example a Teflon® coating (Teflon® is a trademark of DuPont).

Preferably and as depicted, the flexibly deformable top structure 7 is configured as a flexible foil that is sealingly attached to the upper surface 3 of the frame structure 2". The flexible foil preferably is made of an elastomeric material, such as a rubber or a thermoplastic elastomer (TPE) membrane and preferably is sealingly attached to the upper surface 3 of the frame structure 2" by welding. Alternatively, the flexibly deformable top structure 7 is configured as a flexible top portion of the body 2 that is integrated in the frame structure 2" (not shown). In this case, the body material preferably is TPE.

The well 5 of the cartridge 1 shown on the left side comprises a tapered bottom, the bottom declining towards the bottom opening 73. Correspondingly, the front side 74 of the piston 61 is complementarily tapered, so that the piston 61 preferably may abut with its complete front side 74 the bottom of the well 5. This helps ensuring that the top piercing system 60 may be moved into a stable piercing position without the piston 61 bouncing between the side walls of the well 5. Such uncontrolled movement of the piston 61 and the thorn 63 might result in that the thorn 63 unintentionally damages parts of the cartridge 1. Additionally, the efficiency of the release of the liquid reagent or sample 6,6' may be increased, in that the front side 74 of the piston 61 pushes the last leftovers of the liquid towards the bottom opening 73 of the well 5 for the release.

For automatically moving the top piercing system 60 within the well 5, the cartridge 1 comprises an actuating element 41, as it is previously discussed. The actuating element 41 may be guided by a guiding channel 45 (not shown). Such an actuating element 41 is preferably agitated by an agitation mechanism 46, which is controlled by the central control unit 43. Preferably, the agitation mechanism 46 is configured as, or comprises one of a wax pump bladder, a solenoid driven or clamping mechanism driven lever 51, as discussed above. For a precise positioning of the actuating element 41, the piston 61 may comprise on its actuation side 77 a positioning groove 80. This positioning groove 80 is provided by a slight deepening in the surface of the actuation side 77 of the piston 61, which guides the actuating element 41 in an actuation position. Preferably, the positioning groove 80 is located centrally on the actuation side 77 of the piston 61, so that the applied force induces a movement of the piston 61 within the well 5 without risking that the piston 61 is tilted within the well 5 and may then not be moved into the piercing position.

In the embodiment of the top piercing system 60 shown in FIG. 14 on the right side of the cartridge 1, the top piercing system 60 comprise a gasket 62 which provides the seal between the piston 61 and the inner wall of the well 5, as discussed above. The piston 61 with the thorn 63 and the gasket 62 has been moved into the piercing position. Thus, the thorn 63 has already opened the piercable foil 79, and the reagent or sample 6,6' has already partly been pressed out through the bottom opening 73 of the well 5 and through the cover hole 18 of the rigid cover 17 into the gap 12. Here, the top piercing system 60 has been moved manually within the well 5 towards its bottom opening 73 by hand. This is indicated by the finger which is pressed centrally onto the actuation side 77 of the piston 61, so that the top piercing system 60 may be moved toward the bottom opening 73 of the well 5 without being tilted. The piston 61 is not yet abutting the bottom of the well 5 with its front side 74, but pushes the remaining reagent or sample 6,6' towards the bottom opening 73 of the well 5.

The following table provides an overview of materials, thicknesses, and characteristics of the selected components of a cartridge 1, which are suitable for a cartridge 1 in the fifth embodiment according to the present invention:

TABLE 1

| Structure | No | Material | Thickness | Material Characteristic |
|---|---|---|---|---|
| flexible foil | 7 | rubber, silicone rubber, thermoplastic elastomer (TPE) membranes | 0.5-2.0 mm | Elastomeric, impermeable to liquids |
| body | 2 | Cyclic olefin copolymer (COC), cyclic olefin polymer (COP), polypropylene (PP), polystyrene (PS), polycarbonate (PC), glass, acrylic, polytetrafluorethen (PTFE), TPE | 6-25 mm | inert, impermeable to liquids, no interference with liquids |
| piston, thorn | 61 63 | PP, rubber, silicone, acrylic, acrylonitrile-butadiene styrene (ABS) | 7 mm diam. 8 mm height | inert, impermeable to liquids, no interference with liquids |
| piercable foil | 8 79 | polytetrafluorethylene, (PTFE); or foil: aluminum, polyester, polyethylene (PE), PE/PP, vinyl, rayon; hydrophobic polymer: silanes, Teflon ®; sealing material: PS, PP, PVC, PE, PET | 20-100 μm | elastomeric, if required hydrophobic to gap side, low moisture transmission, no interference with liquids |
| thorn relief spacer layer | 64 | gasket material: PET modified with glycol (PETG), natural or synthetic rubber or mixtures thereof, silicone, Teflon ®; acrylic | 0.2-0.7 mm | sealing, no swelling, dimensional stability |
| rigid cover | 17 | polyester foil based on polyethylene terephthalat (Mylar ®), PE, COP, COC, acrylic; electrically conductive coating: indium tin oxide (ITO) | 150 μm-1.8 mm | hydrophobic to gap, optionally electrically conductive, |
| spacers | 9 15 | PETG, FEP, Teflon ®, rubber | 0.3-0.8 mm | inert, impermeable to liquids, no interference with liquids |
| working film | 10 50 | Fluorinated ethylene propylene (FEP), Perfluoralcoxy polymers and copolymers | 8-50 μm | hydrophobic to gap, electrically |

TABLE 1-continued

| Structure | No | Material | Thickness | Material Characteristic |
|---|---|---|---|---|
| | | (PFA), COP, PE, PTFE for electrical insulation: polyimides (PI) such as Kapton ® | | insulating, optionally heat shrinkable |

The invention further relates to a system 40 for liquid droplet manipulation which comprises a substrate 42 with an electrode array 20 and a central control unit 43 for controlling the selection of individual electrodes 44 of the electrode array 43 and for providing the electrodes 44 with individual voltage pulses for manipulating liquid droplets 23 by electrowetting, as discussed above. The preferred system 40 is configured to receive on top of the electrodes 44 the working film 10 of a cartridge 1 according to the present invention comprising at least one top piercing system 60 in one of its wells 5.

The system 40 can be a stand alone and immobile unit, on which a number of operators is working with cartridges 1 that they bring along. The system 40 thus may comprise a number of substrates 42 and a number of electrode arrays 20, so that a number of cartridges 1 can be worked on simultaneously and/or parallel. The number of substrates 42, electrode arrays 20, and cartridges 1 may be 1 or any number between e.g. 1 and 100 or even more; this number e.g. being limited by the working capacity of the central control unit 43. Alternatively, the system 40 can be can be implemented as a hand held which only comprises and is able to work with a single cartridge 1. Every person of skill will understand that intermediate solutions that are situated in-between the two extremes just mentioned will also operate and work within the gist of the present invention.

The system 40 may comprise actuating elements 41 for actuating the at least one top piercing system 60 of a cartridge 1 for releasing reagents, treatment liquids, oil, reaction liquids or sample containing liquids into the gap 12 of the cartridge 1. The substrate 42 may comprise an electrically insulating film, layer or cover 50 that is applied to the electrode array 20, that covers all individual electrodes 44 of the electrode array 20 and that separates the individual electrodes 44 from each other.

The invention also relates to a method of releasing a reagent or sample 6,6' from a well 5 of a cartridge 1 with a working film 10 and at least one piercing element 13 for manipulating samples in liquid droplets with an electrode array 20 when the working film 10 of the cartridge 1 is placed on said electrode array 20. In that method a cartridge is provided which comprises a body 2,2',2" that comprises an upper surface 3, a lower surface 4, and a number of wells 5 configured to hold therein reagents 6 or samples 6'. Each well 5 comprises a top opening 72, and a bottom opening 73 for releasing a liquid from the well 5. The provided cartridge 1 further comprises a piercable bottom structure 8 impermeable to liquids and configured to seal at least one of the bottom openings 73 of the wells 5, and a working film 10 located below the lower surface 4 of the body 2,2',2", the working film 10 being impermeable to liquids and comprising a hydrophobic upper surface 11. The cartridge 1 still further comprises a peripheral spacer 9 located below the lower surface 4 of the body 2,2',2" and connecting the working film 10 to the body 2,2',2", a gap 12 between the lower surface 4 of the body 2,2',2" and the hydrophobic upper surface 11 of the working film 10, the gap 12 being defined by the peripheral spacer 9. The cartridge 1 even further comprises at least one top piercing system 60, each located within at least one of the wells 5 for releasing a reagent or sample 6,6' from said at least one well 5 into the gap 12; wherein each top piercing system 60 comprises a piston 61 and a piercing element 13, the piercing element 13 being configured as a thorn 63 located at a front side 74 of the piston 61. The method includes the further steps of moving the piston 61 within said well 5 toward its bottom opening 73 while providing a seal between the piston 61 and the inner wall of the well 5, piercing the piercable bottom structure 8 with the thorn 63, and releasing a reagent or sample 6,6' from said at least one well 5 into the gap 12 upon moving the piston 61 within the well 5.

Generally, the cartridge 1 as described herein may be used independently of its orientation within the 3-dimensional space. Preferably, the cartridge 1 is used with the gap 12 being oriented horizontally, however, also the cartridge 1 might be oriented vertically or even oriented upside down with the electrode array 20 positioned on top of the gap 12 is possible.

Furthermore, the configuration of the different parts of the cartridge 1, the electrode array 20 and the central control unit 43, and the combination of the different configurations is within the knowledge of the skilled person based on the disclosure and discussion within this document. Thus, as long as a gap 12 is formed for the manipulation of samples in liquid droplet, the gap 12 being enclosed by hydrophobic surfaces, while the electrode array 20 is electrically insulated, and while the bottom opening 73 of a well 5 which comprises a top piercing system 60 is covered by a piercable bottom structure, all combinations of the discussed elements are possible. Were appropriate and necessary, elements as previously discussed e.g. for the related embodiments shown in the FIGS. 1 to 9 may be used exchangeable also in the fifth embodiment according to the present invention of a cartridge comprising the top piercing system 60 as described herein.

The expressions "electrode array", "electrode layout", and "printed circuit board (PCB)" are utilized in this patent application as synonyms.

Any combination of the features of the different embodiments of the cartridge 1 disclosed in this patent application that appear reasonable to a person of skill are comprised by the gist and scope of the present invention.

Even if they are not particularly described in each case, the reference numbers refer to similar elements of the cartridge 1 and system 40 of the present invention.

REFERENCE NUMBERS

| | |
|---|---|
| 1 | cartridge |
| 2, 2', 2" | body |
| 2' | plate-like structure of 2 |
| 2" | frame structure of 2 |
| 3 | upper surface of 2, 2', 2" |
| 4 | lower surface of 2, 2', 2" |
| 5 | well |
| 6 | reagent |
| 6' | sample |
| 7 | flexibly deformable top structure |
| 8 | piercable bottom structure |
| 9 | peripheral spacer |
| 9' | integrated peripheral rim |
| 9" | separate peripheral element |
| 10 | working film |
| 11 | hydrophobic upper surface of 10 |
| 12 | gap |

| | |
|---|---|
| 13 | piercing element |
| 14 | central opening |
| 15 | intermediate spacer |
| 16 | bottom portion |
| 17 | rigid cover |
| 18 | cover hole |
| 19 | cover layer |
| 20 | electrode array |
| 21 | optical fiber |
| 22 | window |
| 23 | droplet |
| 24 | specimen intake |
| 25 | intake recess |
| 25' | alternative intake recess |
| 26 | intake device |
| 27 | cylinder tube |
| 28 | first end of 27 |
| 29 | second end of 27 |
| 30 | plunger |
| 31 | sealing foil |
| 40 | system with 20 |
| 41 | actuating element |
| 42 | substrate |
| 43 | central control unit |
| 44 | individual electrode |
| 45 | guiding channel |
| 46 | agitation mechanism |
| 47 | abutment surface |
| 48 | surface level of 44 |
| 49 | surface of 42 |
| 50 | electrically insulating film, layer or cover |
| 51 | lever |
| 52 | clamping mechanism |
| 53 | outer part of 2 |
| 54 | ground connection |
| 55 | buccal swab head |
| 56 | frit |
| 57 | downward extension of 2 |
| 58 | seal |
| 59 | piercing structure |
| 60 | top piercing system |
| 61 | piston of 60 |
| 62 | gasket of 61 |
| 63 | thorn of 61 |
| 64 | thorn relief spacer layer |
| 65 | through hole of 61 |
| 66 | upper part of 61 |
| 67 | lower part of 61 |
| 68 | longitudinal axis of 63 |
| 69 | neck portion of 63 |
| 70 | tip portion of 63 |
| 71 | relief opening of 64 |
| 72 | top opening of a well |
| 73 | bottom opening of a well |
| 74 | front side of piston |
| 75 | guiding channel of thorn |
| 76 | inner bottom of a well |
| 77 | actuation side of 61 |
| 78 | longitudinal axis of 61 |
| 79 | piercable foil |
| 79' | piercable cover layer |
| 80 | positioning grove of 77 |

What is claimed is:

1. A cartridge (1) with a working film (10) and at least one piercing element (13) for manipulating samples in liquid droplets with an electrode array (20) when the working film (10) of the cartridge (1) is placed on said electrode array (20), wherein the cartridge (1) comprises:
   a) a body (2,2',2") that comprises an upper surface (3), a lower surface (4), and a number of wells (5) configured to hold therein reagents (6) or samples (6'), each well (5) comprising a top opening (72), and a bottom opening (73) for releasing a liquid from the well (5);
   b) a piercable bottom structure (8) impermeable to liquids and configured to seal at least one of the bottom openings (73) of the wells (5);
   c) a working film (10) located below the lower surface (4) of the body (2,2',2"), the working film (10) being impermeable to liquids and comprising a hydrophobic upper surface (11);
   d) a peripheral spacer (9) located below the lower surface (4) of the body (2,2',2") and connecting the working film (10) to the body (2,2',2"); and
   e) a gap (12) between the lower surface (4) of the body (2,2',2") and the hydrophobic upper surface (11) of the working film (10), the gap (12) being defined by the peripheral spacer (9);
   wherein the cartridge (1) further comprises
   f) at least one top piercing system (60), each located within at least one of the wells (5) for releasing a reagent or sample (6,6') from said at least one well (5) into the gap (12);
      wherein each top piercing system (60) comprises a piston (61) and a piercing element (13), the piston (61) being configured to be movable within said well (5) while providing a seal between the piston (61) and the inner wall of the well (5), and the piercing element (13) being configured as a thorn (63) located at a front side (74) of the piston (61) and being configured to pierce the piercable bottom structure (8) for releasing a reagent or sample (6,6') from said at least one well (5) into the gap (12) upon moving the piston (61) within the well (5) toward its bottom opening (73).

2. Cartridge (1) according to claim 1, wherein the piercable bottom structure (8) is configured as a piercable foil (79) that is sealingly attached to the lower surface (4) of the body (2,2',2").

3. Cartridge (1) according to claim 2, wherein the piercable foil (79) is sized to seal the bottom openings (73) of all wells (5) of the body (2,2',2").

4. Cartridge (1) according to claim 1, wherein a front side (74) of the piston (61) of the at least one top piercing system (60) is adapted in shape to a shape of an inner bottom (76) of the well (5) into which the at least one top piercing system (60) is integrated.

5. Cartridge (1) according to claim 4, wherein the inner bottom (76) of the well (5) which comprises the at least one top piercing system (60) is configured as a taper-bottom, and wherein the front side (74) of the piston (61) of said at least one top piercing system (60) is configured as a complementary tapered front side (74).

6. Cartridge (1) according to claim 4, wherein the inner bottom (76) of the well (5), which comprises the at least one top piercing system (60) is configured as a flat bottom, and wherein the front side (74) of the piston (61) of said at least one top piercing system (60) is configured as a complementary flat front side (74).

7. Cartridge (1) according to claim 1, wherein the thorn (63) comprises a neck portion (69) and a tip portion (70) with the tip, the tip portion (70) being configured to pierce the piercable bottom structure (8).

8. Cartridge (1) according to claim 1, wherein the thorn (63) comprises at least one guiding channel (75) for providing an outlet path for releasing the reagent or sample (6,6') from the well (5) when the thorn (63) of the top piercing system (60) has pierced the piercable bottom structure (8).

9. Cartridge (1) according to claim 7, wherein the tip (70) of the thorn (63) is Phillips head shaped.

10. Cartridge (1) according to claim 1, wherein the top piercing system (60) comprises at least one gasket (62)

attached to an upper part (66) of the piston (61) for sealingly abutting the inner wall of the well (5).

11. Cartridge (1) according to claim 10, wherein the at least one gasket (62) is an O-ring, or a quad-ring, or a bellow.

12. Cartridge (1) according to claim 1, wherein the piston (61) and the thorn (63) of the top piercing system (60) are made as a single injection molded piece.

13. Cartridge (1) according to claim 1, wherein the cartridge (1) further comprises a thorn relief spacer layer (64) that is attached to a lower side of the piercable bottom structure (8) and that comprises a relief opening (71) situated below the bottom opening (73) of the well (5), said relief opening (71) providing an additional space for the thorn (63) after piercing the piercable bottom structure (8), and providing an outlet path for releasing the reagent or sample (6,6') into the gap (12).

14. Cartridge (1) according to claim 13, further comprising a rigid cover (17) that is attached to a lower side of the thorn relief spacer layer (64), said rigid cover (17) enclosing the gap (12) on a side opposite to the working film (10) and comprising at least one cover hole (18) which is situated below the bottom opening (73) of the well (5) and below the relief opening (71) of the thorn relief spacer layer (64).

15. Cartridge (1) of claim 1, wherein the peripheral spacer (9) surrounds a part or the entire foot print of the cartridge (1) and is attached to the lower surface (4) of the piercable bottom structure (8).

16. Cartridge of claim 15, wherein the cartridge (1) comprises at least one intermediate spacer (15) configured reaching from the peripheral spacer (9) of one side of the cartridge (1) to the peripheral spacer (9) of another side of the cartridge (1) or as a separate element located within the area of the gap (12), the intermediate spacer (15) being attached to the lower surface (4) of the piercable bottom structure (8).

17. The cartridge of claim 1, wherein the working film (10) is configured as a monolayer of a hydrophobic material.

18. The cartridge of claim 1, wherein the working film (10) is configured as a monolayer of electrically non-conductive material, the upper surface (11) of the working film (10) being treated to be hydrophobic.

19. A system (40) for liquid droplet manipulation, the system comprising a substrate (42) with an electrode array (20) and a central control unit (43) for controlling the selection of individual electrodes (44) of the electrode array (20) and for providing the electrodes (44) with individual voltage pulses for manipulating liquid droplets (23) by electrowetting, wherein the system (40) is configured to receive on top of the electrodes (44) a cartridge (1) with a working film (10) and at least one piercing element (13) for manipulating samples in liquid droplets with an electrode array (20) when the working film (10) of the cartridge (1) is placed on said electrode array (20), wherein the cartridge (1) comprises:
  a) a body (2,2',2") that comprises an upper surface (3), a lower surface (4), and a number of wells (5) configured to hold therein reagents (6) or samples (6'), each well (5) comprising a top opening (72), and a bottom opening (73) for releasing a liquid from the well (5);
  b) a piercable bottom structure (8) impermeable to liquids and configured to seal at least one of the bottom openings (73) of the wells (5);
  c) a working film (10) located below the lower surface (4) of the body (2,2',2"), the working film (10) being impermeable to liquids and comprising a hydrophobic upper surface (11);
  d) a peripheral spacer (9) located below the lower surface (4) of the body (2,2',2") and connecting the working film (10) to the body (2,2',2"); and
  e) a gap (12) between the lower surface (4) of the body (2,2',2") and the hydrophobic upper surface (11) of the working film (10), the gap (12) being defined by the peripheral spacer (9);
  wherein the cartridge (1) further comprises
  f) at least one top piercing system (60), each located within at least one of the wells (5) for releasing a reagent or sample (6,6') from said at least one well (5) into the clap (12);
    wherein each top piercing system (60) comprises a piston (61) and a piercing element (13), the piston (61) being configured to be movable within said well (5) while providing a seal between the piston (61) and the inner wall of the well (5), and the piercing element (13) being configured as a thorn (63) located at a front side (74) of the piston (61) and being configured to pierce the piercable bottom structure (8) for releasing a reagent or sample (6,6') from said at least one well (5) into the gap (12) upon moving the piston (61) within the well (5) toward its bottom opening (73).

20. The system of claim 19, wherein the system (40) comprises actuating elements (41) for actuating the piston (61) of at least one top piercing system (60) of a cartridge (1) for releasing reagents, treatment liquids, oil, reaction liquids or sample containing liquids into the gap (1 2) of the cartridge (1).

21. The system of claim 19, wherein the substrate (42) comprises an electrically insulating film, layer or cover (50) that is applied to the electrode array (20), that covers all individual electrodes (44) of the electrode array (20) and that separates the individual electrodes (44) from each other.

22. A method of releasing a reagent or sample (6,6') from a well (5) of a cartridge (1) with a working film (10) and at least one piercing element (13) for manipulating samples in liquid droplets with an electrode array (20) when the working film (10) of the cartridge (1) is placed on said electrode array (20), wherein the method comprises the following steps:
  providing a cartridge (1) which comprises:
    a) a body (2,2',2") that comprises an upper surface (3), a lower surface (4), and a number of wells (5) configured to hold therein reagents (6) or samples (6'), each well (5) comprising a top opening (72), and a bottom opening (73) for releasing a liquid from the well (5);
    b) a piercable bottom structure (8) impermeable to liquids and configured to seal at least one of the bottom openings (73) of the wells (5);
    c) a working film (10) located below the lower surface (4) of the body (2,2',2"), the working film (10) being impermeable to liquids and comprising a hydrophobic upper surface (11);
    d) a peripheral spacer (9) located below the lower surface (4) of the body (2,2',2") and connecting the working film (10) to the body (2,2',2");
    e) a gap (12) between the lower surface (4) of the body (2,2',2") and the hydrophobic upper surface (11) of the working film (10), the gap (12) being defined by the peripheral spacer (9); and
    f) at least one top piercing system (60), each located within at least one of the wells (5) for releasing a reagent or sample (6,6') from said at least one well (5) into the gap (12); wherein each top piercing system (60) comprises a piston (61) and a piercing element (13), the piercing element (13) being configured as a thorn (63) located at a front side (74) of the piston (61);

moving the piston (61) within said well (5) toward its bottom opening (73) while providing a seal between the piston (61) and the inner wall of the well (5);

piercing the piercable bottom structure (8) with the thorn (63); and releasing a reagent or sample (6,6') from said at least one well (5) into the gap (12) upon moving the piston (61) within the well (5).

23. A system configured to perform a method of releasing a reagent or sample (6,6') from a well (5) of a cartridge (1) with a working film (10) and at least one piercing element (13) for manipulating samples in liquid droplets with an electrode array (20) when the working film (10) of the cartridge (1) is placed on said electrode array (20), wherein the method comprises the following steps:

providing a cartridge (1) which comprises:
   a) a body (2,2',2") that comprises an upper surface (3), a lower surface (4), and a number of wells (5) configured to hold therein reagents (6) or samples (6'), each well (5) comprising a top opening (72), and a bottom opening (73) for releasing a liquid from the well (5);
   b) a piercable bottom structure (8) impermeable to liquids and configured to seal at least one of the bottom openings (73) of the wells (5);
   c) a working film (10) located below the lower surface (4) of the body (2,2',2"), the working film (10) being impermeable to liquids and comprising a hydrophobic upper surface (11);
   d) a peripheral spacer (9) located below the lower surface (4) of the body (2,2',2") and connecting the working film (10) to the body (2,2',2");
   e) a gap (12) between the lower surface (4) of the body (2,2',2") and the hydrophobic upper surface (11) of the working film (10), the gap (12) being defined by the peripheral spacer (9); and
   f) at least one top piercing system (60), each located within at least one of the wells (5) for releasing a reagent or sample (6,6') from said at least one well (5) into the gap (12); wherein each top piercing system (60) comprises a piston (61) and a piercing element (13), the piercing element (13) being configured as a thorn (63) located at a front side (74) of the piston (61);

moving the piston (61) within said well (5) toward its bottom opening (73) while providing a seal between the piston (61) and the inner wall of the well (5);

piercing the piercable bottom structure (8) with the thorn (63); and releasing a reagent or sample (6,6') from said at least one well (5) into the gap (12) upon moving the piston (61) within the well (5).

* * * * *